(12) United States Patent
Isgrò et al.

(10) Patent No.: US 9,578,959 B2
(45) Date of Patent: *Feb. 28, 2017

(54) LABORATORY TABLE HAVING TABLETOP ELEMENTS

(71) Applicant: TECAN Trading AG, Männedorf (CH)

(72) Inventors: Claudio Isgrò, Dürnten (CH); Theo Meier, Hombrechtikon (CH); Dominic Erb, Winterthur (CH); Beat Bolli, Männedorf (CH)

(73) Assignee: TECAN TRADING AG, Mannedorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,745

(22) Filed: Jun. 15, 2015

(65) Prior Publication Data

US 2015/0272318 A1    Oct. 1, 2015

Related U.S. Application Data

(63) Continuation-in-part of application No. 14/055,550, filed on Oct. 16, 2013, now Pat. No. 9,060,598, which
(Continued)

(30) Foreign Application Priority Data

Jul. 21, 2011    (CH) ...................................... 1219/11

(51) Int. Cl.
*A47B 13/00* (2006.01)
*A47B 13/08* (2006.01)
(Continued)

(52) U.S. Cl.
CPC .............. *A47B 13/088* (2013.01); *B01L 9/02* (2013.01); *F16B 1/00* (2013.01);
(Continued)

(58) Field of Classification Search
CPC .............................. A47B 13/003; A47B 13/08
USPC ............ 108/157.18, 157.17, 157.15, 159.11, 108/157.1, 157.16, 158.13, 158.12; 248/188
See application file for complete search history.

(56) References Cited

U.S. PATENT DOCUMENTS 795,957 A * 8/1905 Cartland ............ A47B 88/0044
108/157.16
1,793,709 A * 2/1931 Meyers ................... F16B 12/48
108/157.16
(Continued)

FOREIGN PATENT DOCUMENTS

JP    8131852 A1    5/1996
JP    11137344 A1   5/1999

*Primary Examiner* — Jose V Chen
(74) *Attorney, Agent, or Firm* — Motaro, Michalos & Zaccaria P.C.

(57) ABSTRACT

Laboratory table with front and opposite rear frame parts, has replaceable tabletop elements positionable thereon. In a first variant, the laboratory table further has detent openings at regular distances on the front and/or rear frame parts, defining a modular grid. Each opening can receive a detent bolt of a modular tabletop element, each element having at least two detent bolts for the insertion into one of the detent openings. In a second variant, each tabletop element has at least one detent opening on a front and/or rear side of the tabletop element, for insertion of a detent bolt. The front and/or rear frame part of the laboratory table have detent bolts arranged at a regular distance defining a modular grid, each one of the detent bolts being for insertion into one of the detent openings of the tabletop elements positioned on these front and rear frame parts.

36 Claims, 8 Drawing Sheets

Related U.S. Application Data is a continuation-in-part of application No. 13/550,900, filed on Jul. 17, 2012, now Pat. No. 8,584,602.

(51) Int. Cl.
  *F16B 1/00* (2006.01)
  *B01L 9/02* (2006.01)
  *A47B 37/00* (2006.01)
  *G01N 35/00* (2006.01)

(52) U.S. Cl.
  CPC ... *A47B 2037/005* (2013.01); *B01L 2200/025* (2013.01); *B01L 2200/028* (2013.01); *B01L 2300/0829* (2013.01); *F16B 2001/0035* (2013.01); *G01N 2035/00306* (2013.01)

(56) References Cited

U.S. PATENT DOCUMENTS

| | | | | |
|---|---|---|---|---|
| 1,795,138 A * | 3/1931 | Ohnstrand | ........... | A47B 13/003 108/157.15 |
| 2,973,233 A * | 2/1961 | McPhee | ................. | F16B 12/48 248/188 |
| 3,267,889 A * | 8/1966 | Bedol | ...................... | A47B 3/02 108/118 |
| 4,317,416 A * | 3/1982 | Baum | ..................... | F16B 12/22 108/157.1 |
| 4,944,235 A * | 7/1990 | Jahnke | ................. | A47B 13/003 108/154 |
| 5,232,303 A * | 8/1993 | Rubner | ................ | A47B 13/021 248/188 |
| 5,549,055 A * | 8/1996 | Kusch | .................. | A47B 13/003 108/115 |
| 6,082,838 A * | 7/2000 | Bissu-Palombo | ........ | A47B 3/12 108/115 |
| 6,250,842 B1 * | 6/2001 | Kruger | ............... | B60N 2/01575 297/335 |
| 6,318,276 B1 * | 11/2001 | Reinecke | ............. | A47B 87/002 108/158.13 |
| 7,128,493 B2 * | 10/2006 | Alarcon-Lopez | ....... | F16B 12/20 403/315 |
| 8,584,602 B2 * | 11/2013 | Isgro | ........................ | B01L 9/02 108/157.1 |
| 9,060,598 B2 * | 6/2015 | Isgro | .................... | A47B 13/088 |
| 2010/0282133 A1 | 11/2010 | Wong | | |

\* cited by examiner

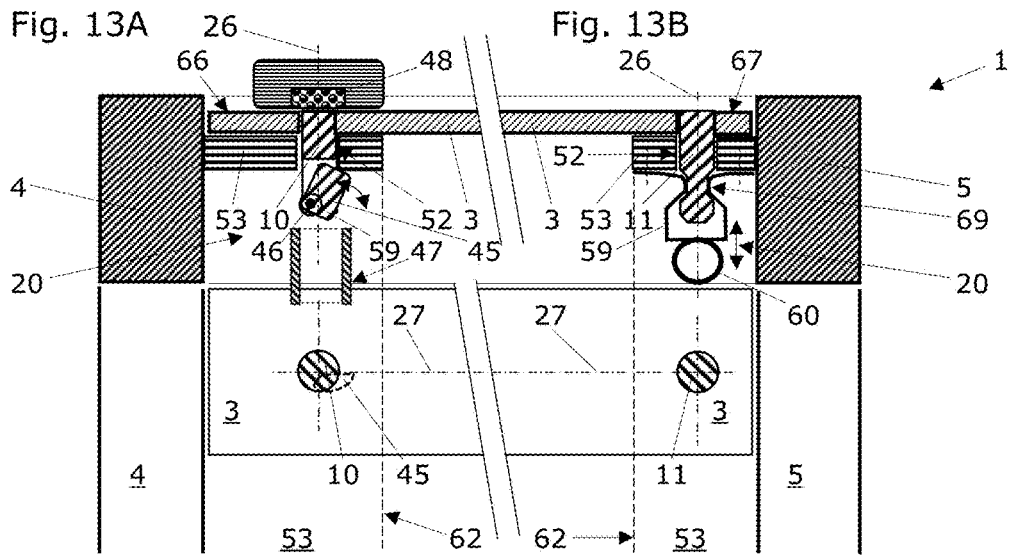

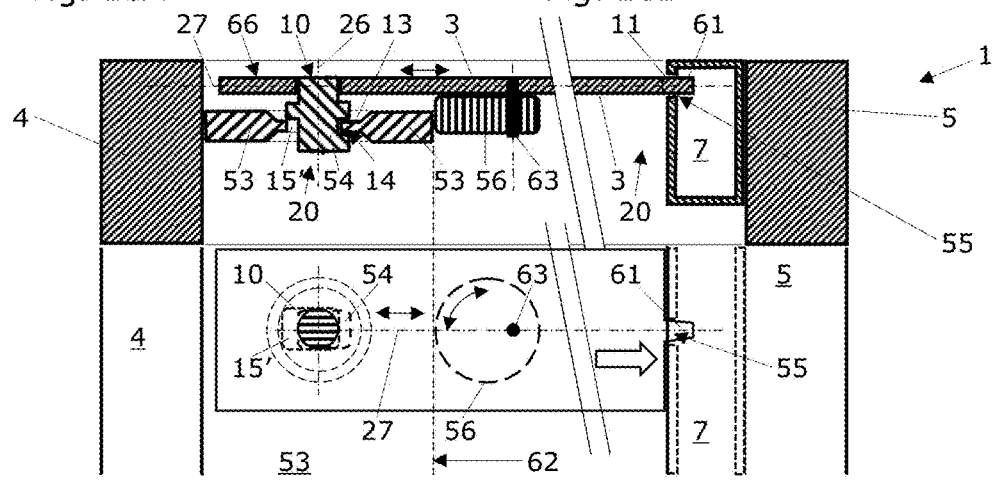

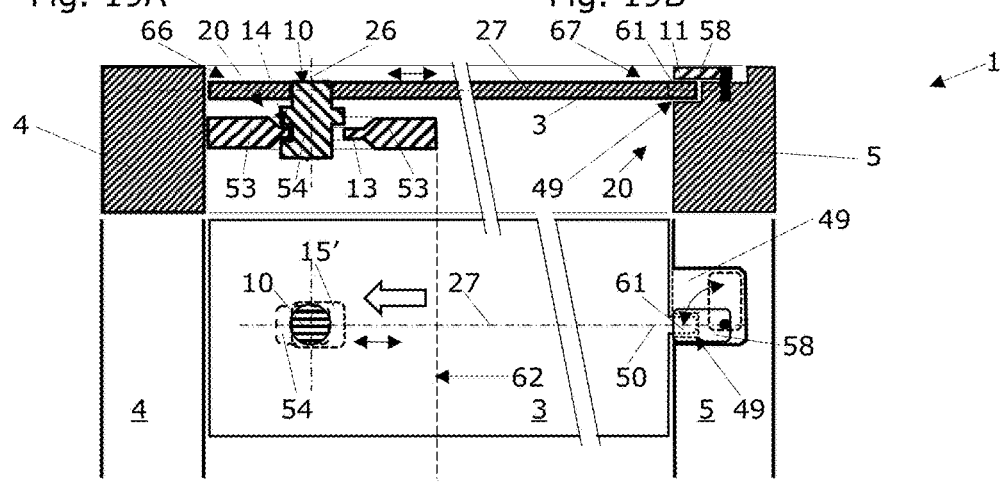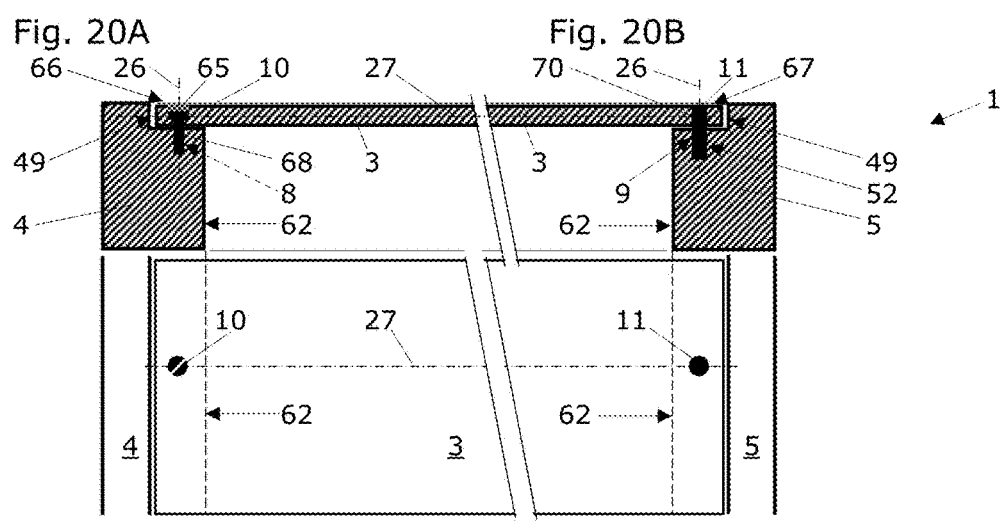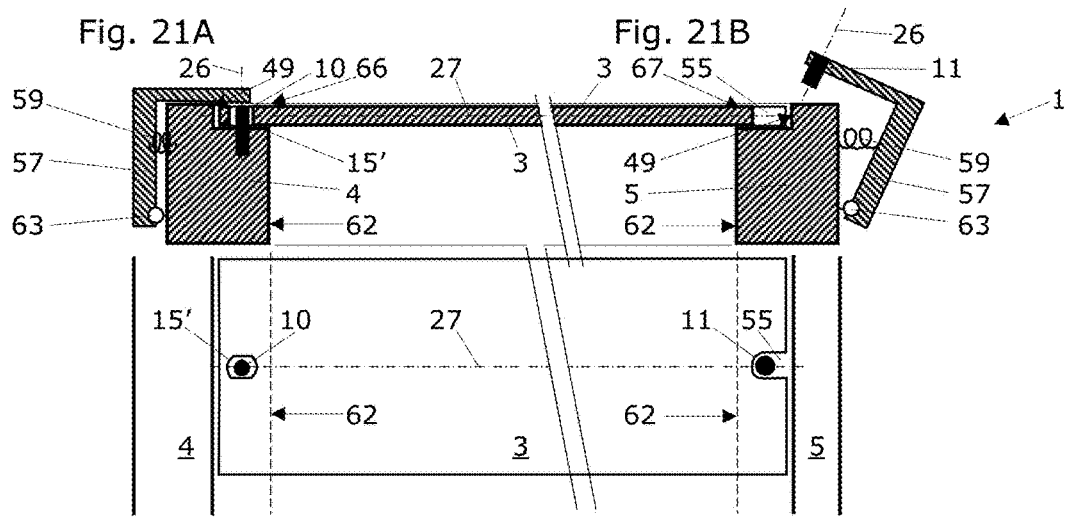

LABORATORY TABLE HAVING TABLETOP ELEMENTS

RELATED PATENT APPLICATIONS

This patent application is a Continuation In Part Application of the Continuation In Part U.S. application Ser. No. 14/055,550 filed on Oct. 16, 2013 and claiming priority of the U.S. application Ser. No. 13/550,900, filed on Jul. 17, 2012 and granted as U.S. Pat. No. 8,584,602 B2, and claiming priority of the Swiss Patent Application No. 01219/11 filed on Jul. 21, 2011. The entire disclosure of all these applications is herein incorporated by explicit reference for any purpose.

TECHNICAL FIELD OF THE INVENTION

The invention relates to a laboratory table, in particular for automated laboratory systems, which comprises at least a front frame part and a rear frame part opposite thereto, as well as a number of tabletop elements positionable on these front and rear frame parts.

Large laboratory facilities, in particular automated laboratory systems, typically comprise a base frame, on which a laboratory tabletop is laid. This laboratory tabletop is used as a work surface for the robot arms, which access the laboratory tabletop from above. The robot arms are typically provided with pipette tips for the transport of liquids or with grippers for the transport of labware, e.g., microplates or sample tubes. The Freedom EVO® Liquid Handling Workstation of the current applicant is mentioned as an example of such a laboratory system. The space below the work surface is often also to be able to be used for additional apparatus, such as centrifuges, incubators, microplate readers, etc. For this purpose, for example, openings are sawn into the tabletop, so that robot arms can access the apparatus below the work surface for the transport of labware (e.g., for loading and unloading of a centrifuge).

RELATED PRIOR ART

Apparatus such as microplate incubators, polymerase chain reaction (PCR) thermocyclers for the amplification of nucleic acids, and solid phase extraction (SPE) modules having comparatively large overall height are frequently located on the work surfaces of such "liquid handling workstations" or "robotic sample processors" (RSP). Some of these apparatuses are so tall that the pipette tips installed on the robot arms can no longer be moved over them. The apparatuses must therefore be detoured as obstructions. If tall apparatuses can be placed on a second, lower work surface, the direct travel routes of the robot arms having pipette tips or grippers remain free.

Very precise alignment of the pipette tips on the robot arm to the wells of the microplates on the work surface is necessary for pipetting in microplates having 384 wells (center-to-center distance 4.5 mm) or 1526 wells (center-to-center distance 2.25 mm). Continuous laboratory tabletops are often provided with detent cams or other holders for positioning so-called "carriers", which carry the labware, e.g., microplates, in order to achieve the required positioning precision.

Laboratory tables having tabletop elements are known from the prior art. According to JP 11-137 344 A1, for example, this relates to the use of office desks as laboratory tables, four office desks being arranged and held by means of a frame in a rectangle and a laboratory tabletop being laid on this frame.

A laboratory table is known from JP 8-131 852 A1, in which no wiring is visible or can obstruct the use of the laboratory table. The worktop of this laboratory table consists of a front part and a rear part, which each rest on a frame corresponding to the size of these partial worktops. The cables for the required electrical connections can be laid in special cable channels.

From US 2010/0282133 A1 a modular welding table is known that comprises a plurality of legs, two of which legs being connected by a horizontal bar in each case; a plurality of bars that define the width of the welding table and that are evenly spaced by gaps out across the length of said horizontal bar; a plurality of seats being evenly spaced out along the length of each of said bars and having at least one fastening hole facing up; and a plurality of plates having matching holes to the seat's fastening holes, the plates being spaced by a groove and arranged in parallel to each other in each case and the plates waving a width that fits the gaps in-between the bars.

OBJECTS AND SUMMARY OF THE PRESENT INVENTION

The object of the present invention is to propose an alternative laboratory table, which comprises at least a front frame part and a rear frame part opposite thereto, as well as tabletop elements positionable on these front and rear frame parts.

This object is achieved according to a first aspect and according to a second aspect in that two different types of laboratory tables having the features as herein disclosed are proposed.

Further features according to the invention result from the dependent claims.

Advantages of the laboratory table according to the invention comprise:

- Simple laboratory devices can be equipped with individual or a few tabletop elements.
- Larger laboratory devices up to complex laboratory facilities, e.g., so-called "liquid handling workstations" or "robotic sample processors" (RSP) can be equipped with a number of modular tabletop elements.
- The modular tabletop elements according to the invention are arbitrarily replaceable and exchangeable in or on frame parts equipped according to the invention.
- The replaceable tabletop elements can very especially comprise equipment and/or structures, so that areas of the work surface of laboratory devices or laboratory facilities can be assigned permanently or also only temporarily to specific workflows.
- If a level formed by the installed tabletop elements is defined as the main work level in a large laboratory device or in a complex laboratory facility, additional secondary work levels can be defined above and/or below this main work level and can be equipped with further tabletop elements.
- By lowering the tabletop elements to a lower secondary work level, components having a taller installation height can be installed in laboratory facilities, so that the movement range of robots present in these laboratory facilities is impaired substantially less.
- Selected areas of the work surface of laboratory devices or laboratory facilities can be left open or equipped with tabletop elements, which have corresponding reach-through openings, to allow the transfer of containers (e.g., for loading/unloading a centrifuge).

Areas having lower work surface adjacent to or between work surfaces of the upper level can be modularly assembled from various existing tabletop elements.

Individual tabletop elements which can be inlaid naturally result in greater tolerances than continuous laboratory tabletops. Mechanical tolerances can add up in an unfavorable manner in this case. Therefore, the tabletop elements are preferably fixed by fixing to the frame parts.

By clamping a frame part using a stop surface in a detent rail/detent bolt combination and using the clamping bow of a clamping lever, a friction-locked, blocked fixing of the detent bolt results, without the frame of the laboratory device or the laboratory facility being tensioned or even deformed. The special equipment and/or structures of the tabletop elements and therefore also containers placed on this equipment and/or these structures are preferably positioned exactly.

For every configuration of the automated laboratory system in which the apparatuses are located below the work surface at another location, another laboratory tabletop having altered opening is necessary. The number of the laboratory tabletop variants rapidly becomes larger and larger. Through skilled combination of individual tabletop elements and laboratory table elements, which are of different widths under certain circumstances, having openings, all variants of work surfaces can be modularly assembled.

The modularity of the tabletop elements in combination with the modular grid of the fastening of the detent cams on the tabletop elements and the division of the detent openings in the detent rails allows an arbitrary selection and replaceability of the tabletop elements, so that existing laboratory facilities can also be adapted easily for other intended uses.

A variety of detent bolts or detent pins may be applied for reversibly but safely fixing the modular tabletop elements on the front frame part and/or on the rear frame part or on the frame of the laboratory table.

A variety of fixing mechanisms are proposed for reversibly but safely and individually fixing single modular tabletop elements positioned on the front and rear frame part of the laboratory table.

A variety of fixing mechanisms are proposed for reversibly but safely and commonly fixing a number or multitude of modular tabletop elements positioned on the front and rear frame part of the laboratory table.

BRIEF INTRODUCTION OF THE ATTACHED DRAWINGS

The laboratory table according to the invention will be explained in greater detail on the basis of the appended drawings, these drawings showing exemplary embodiments and not restricting the scope of the present invention. In the figures.

Figure 5A:
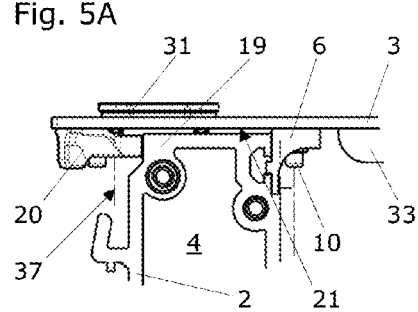
FIG. 5A-5B shows detail sections of FIG. 4.
Figure 5B:
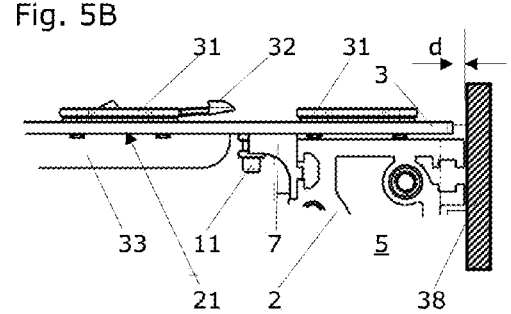
Figure 6A:
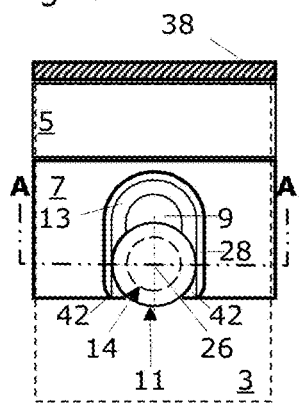
Figure 6B:
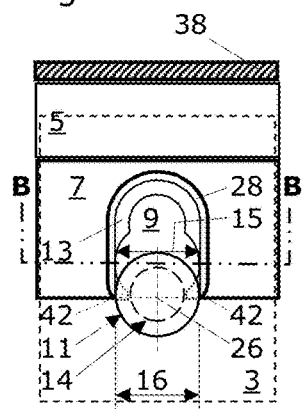
Figure 6C:
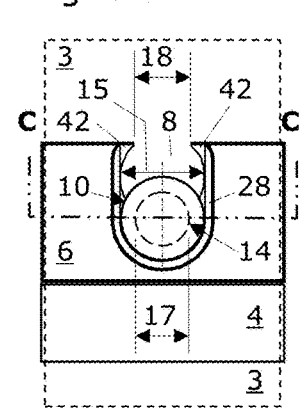
Figure 7A:
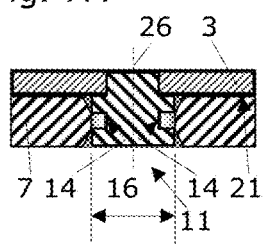
Figure 7B:
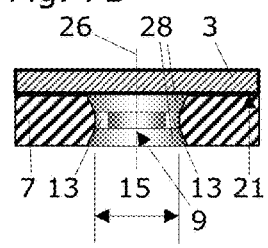
Figure 7C:
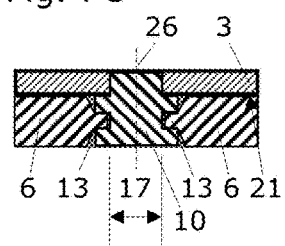
Figure 8A:
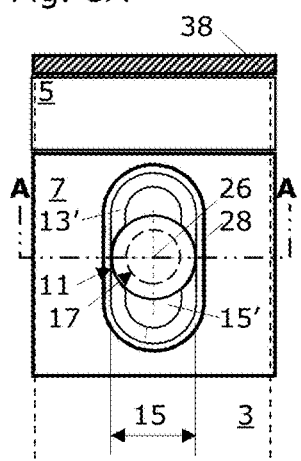
Figure 8B:
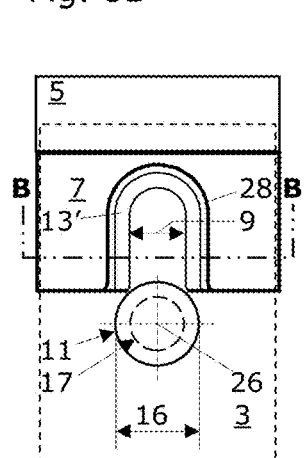
Figure 8C:
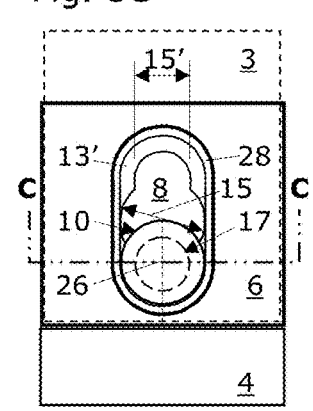
Figure 9A:
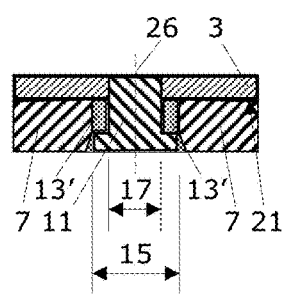
Figure 9B:
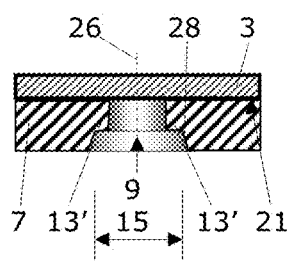
Figure 9C:
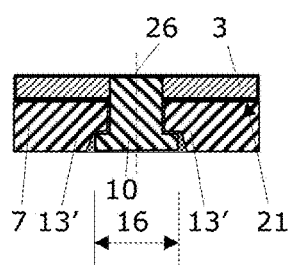
Figure 10A:
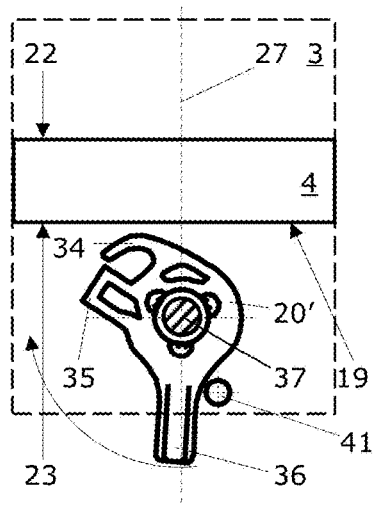
Figure 10B:
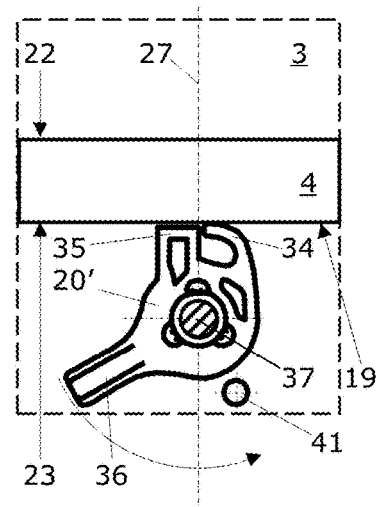

FIG. 5A showing a vertical section through the upper part of the front frame part having detent rail, stop surface, and tabletop element having clamping lever, and FIG. 5B showing a vertical section through the upper part of the rear frame part having detent rail and detent bolt;

FIG. 6A-6C shows detail views of a detent rail/detent bolt combination according to a first embodiment variant:

FIG. 6A showing the detent bolt upon countersinking into the rear upper detent rail during the installation of the tabletop element, FIG. 6B showing the detent bolt in a fixing position in the rear upper detent rail, in which it is fixed, and FIG. 6C showing the detent bolt in an end position in which it is fixed blocked in the front upper detent rail;

FIG. 7A-7C shows detail sections through the detent rail/detent bolt combination according to the first embodiment variant of FIG. 6A-6B:

FIG. 7A showing the detent bolt placed in the recess of the detent rail during the installation of the tabletop element, FIG. 7B showing the detent opening behind the detent bolt, and FIG. 7C showing the detent bolt in an end position in which it is fixed blocked in the front upper detent rail;

FIG. 8A-8C shows detail views of a detent rail/detent bolt combination according to a second and third embodiment variant:

FIG. 8A showing the detent bolt upon countersinking in the rear upper detent rail according to a second embodiment variant during the installation of the tabletop element, FIG. 8B showing the detent bolt upon insertion into the rear upper detent rail according to a third embodiment variant during the installation of the tabletop element, and FIG. 8C showing the detent bolt in an end position, in which it is fixed blocked in the front upper detent rail according to a second embodiment variant;

FIG. 9A-9C shows detail sections through the detent rail/detent bolt interaction according to the second and third embodiment variants of FIG. 8A-8C:

FIG. 9A showing the detent bolt placed in the recess of the detent rail during the installation of the tabletop element, FIG. 9B showing the detent opening behind the detent bolt, and FIG. 9C showing the detent bolt in an end position, in which it is fixed blocked in the front upper detent rail;

FIG. 10A-10B shows detail views of a clamping lever/stop surface interaction in the upper tabletop level:

FIG. 10A showing the clamping lever in the open position, and

Figure 11A:
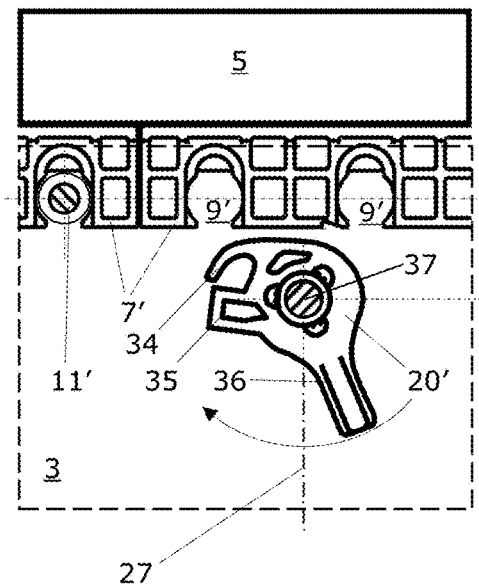
Figure 11B:
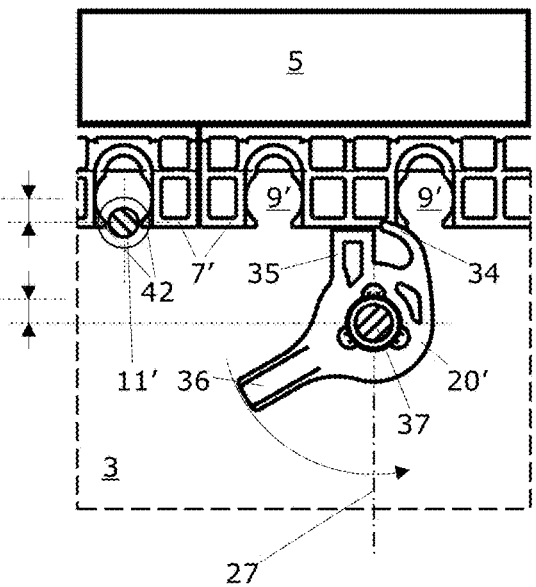

FIG. 10B showing the clamping lever in the locked position;

FIG. 11A-11B shows detail views of a clamping lever/detent rail interaction in the lower tabletop level:

FIG. 11A showing the clamping lever in the open position, and

Figure 12A:
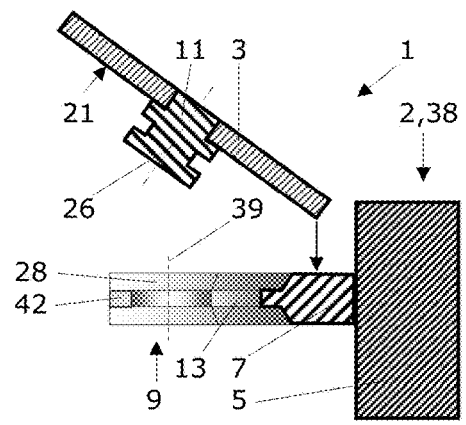
Figure 12B:
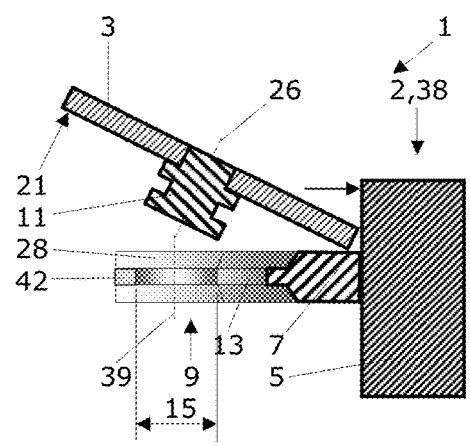
Figure 12C:
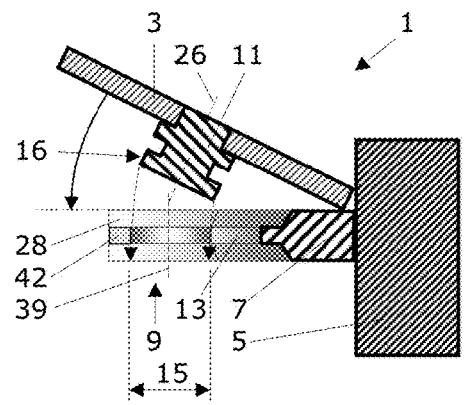
Figure 12D:
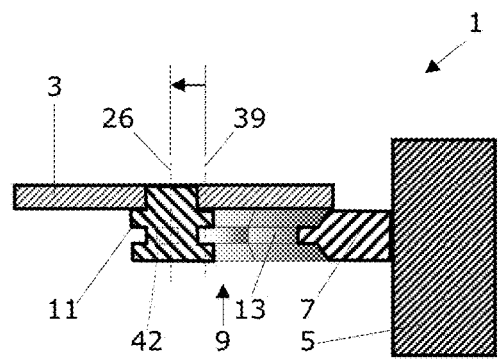
Figure 12E:
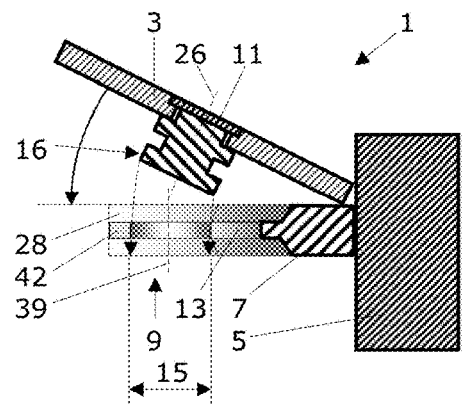
Figure 12F:
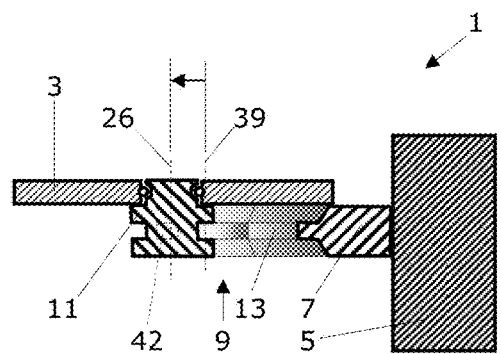

FIG. 11B showing the clamping lever in the locked position;

FIG. 12A-12F shows detail views through a rear detent rail upon installation of the tabletop element:

FIG. 12A showing the first step of inlaying a tabletop element with application of a detent bolt to the rear detent rail according to a first embodiment;

FIG. 12B showing the second step of inlaying the tabletop element with additional application of the detent bolt to a rear stop according to the first embodiment;

FIG. 12C showing the third step of inlaying the tabletop element with pivoting into the horizontal while simultaneously applying the detent bolt to the rear detent rail and the rear stop according to the first embodiment;

FIG. 12D showing the fourth step of inlaying the tabletop element with horizontal displacement and fixing of the tabletop element using the detent bolt according to the first embodiment;

FIG. 12E showing the third step of inlaying the tabletop element with pivoting into the horizontal while simultaneously applying a detent bolt to the rear detent rail and the rear stop according to a second embodiment; and FIG. 12F showing the fourth step of inlaying the tabletop element with horizontal displacement and fixing of the tabletop element using a detent bolt according to a third embodiment;

FIG. 13A-13B shows vertical section and top views of first and second additional embodiments of detent bolts and fixing mechanisms:

FIG. 13A showing a detent bolt that comprises a fixing mechanism configured as a flip part;

FIG. 13B showing a detent bolt that comprises a turned down portion which is implemented to be acted on by at least one spring;

FIG. 14A-14B shows vertical section and top views of third and fourth additional embodiments of detent bolts and fixing mechanisms:

FIG. 14A showing a detent bolt positioned below the replaceable tabletop element and comprising magnetizable material or a magnet;

FIG. 14B showing a detent bolt positioned below the replaceable tabletop element and being configured to be movable with respect to the replaceable tabletop element and in direction of the bolt axis;

FIG. 15A-15B shows vertical section and top views of fifth and sixth additional embodiments of detent bolts and fixing mechanisms:

FIG. 15A showing a detent bolt that is rotatably attached to the tabletop element and comprising a key element configured for insertion into an oblong hole;

FIG. 15B showing a detent bolt that is immovably positioned below the replaceable tabletop element and configured for horizontal insertion into a slit;

FIG. 16A-16B shows vertical section and top views of seventh and eighth additional embodiments of detent bolts and fixing mechanisms:

FIG. 16A showing a detent bolt immovably extending perpendicular to the replaceable tabletop element and comprising a key element configured for insertion into an oblong hole;

FIG. 16B showing a detent bolt implemented as nose extension of the tabletop element and a fixing mechanism configured as an eccentric lock element;

FIG. 17A-17B shows vertical section and top views of ninth and tenth additional embodiments of detent bolts and fixing mechanisms:

FIG. 17A showing a fixing mechanism configured as a lock profile for displacing all present replaceable tabletop elements in direction of the tabletop axis;

FIG. 17B showing a detent bolt implemented as nose extension of a replaceable tabletop element and configured for horizontal insertion into a slit;

FIG. 18A-18B shows vertical section and top views of eleventh and twelfth additional embodiments of detent bolts and fixing mechanisms:

FIG. 18A showing a detent bolt immovably extending perpendicular to the replaceable tabletop element and comprising a key element configured for insertion into an oblong hole;

FIG. 18B showing a fixing mechanism configured as a lock slide which in a locking position abuts a detent bolt and thus blocks the replaceable tabletop element in direction of the tabletop axis;

FIG. 19A-19B shows vertical section and top views of thirteenth and fourteenth additional embodiments of detent bolts and fixing mechanisms:

FIG. 19A showing a detent bolt immovably extending perpendicular to the replaceable tabletop element and comprising a key element configured for insertion into an oblong hole;

FIG. 19B showing a detent opening configured as cut-out part which is implemented for receiving a nose extension of a replaceable tabletop element;

FIG. 20A-20B shows vertical section and top views of fifteenth and sixteenth additional embodiments of detent bolts and fixing mechanisms:

FIG. 20A showing a detent bolt implemented as a screw captive incorporated to the replaceable tabletop element;

FIG. 20B showing a detent bolt implemented as a pin captive attached to the replaceable tabletop element;

FIG. 21A-21B shows vertical section and top views of seventeenth and eighteenth additional embodiments of detent bolts and fixing mechanisms:

FIG. 21A showing a detent opening of a tabletop element configured as oblong hole that extends at a side of the tabletop element, a detent bolt arranged on a frame part, and a fixing mechanism configured as a tiltable lock profile;

FIG. 21B showing a detent opening of a tabletop element configured as slit that extends from a side of the tabletop element, a detent bolt arranged on a fixing mechanism configured as a tiltable lock profile.

DETAILED DESCRIPTION OF THE PRESENT INVENTION

Figure 1:
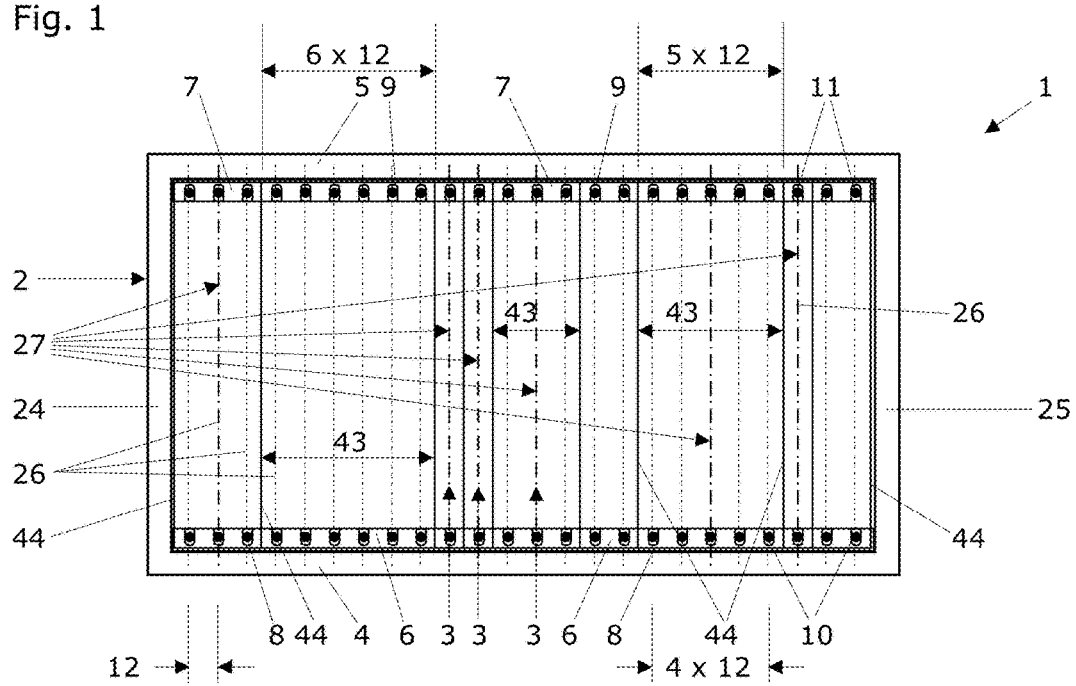
FIG. 1 shows a top view of a laboratory table according to a first embodiment having a number of tabletop elements installed in an intermediate space of the frame.

FIG. 1 shows a top view of a laboratory table 1 according to a first embodiment having a number of tabletop elements 3 installed in an intermediate space of the frame 2. This laboratory table 1 comprises at least one frame 2 having a front frame part and a rear frame part 4,5 opposite thereto as well as tabletop elements 3 positionable on this at least one frame 2. The frame parts 4,5 arranged opposite to one another are preferably arranged parallel to one another and it is also preferable for the frame 2 to comprise two further frame parts 24,25 and to be implemented as a rectangular frame. The tabletop elements 3 of the laboratory table 1 are preferably smaller in at least one horizontal dimension than the frame 2 according to a first embodiment. Tabletop elements 3 of the laboratory table 1 according to a first embodiment, which are smaller in all horizontal dimensions than the frame 2, are also preferred. In addition, the following variants of the arrangement of the tabletop elements in relation to the frame supporting these tabletop elements are preferable as needed:

the tabletop elements are located at a higher level than the uppermost frame surface;

the surface of the tabletop elements is flush with the uppermost frame surface;

the tabletop elements are located at a lower level than the uppermost frame surface.

In particular the first-mentioned variant allows the provision of a laboratory table 1 having a completely flat surface.

In addition, it can be provided for smaller laboratory devices that the frame is smaller than the individual tabletop element, which can protrude beyond the frame on at least one side or also on all sides. Replaceable tabletop elements can also be used in the case of simple laboratory devices. These tabletop elements can comprise very special equipment and/or structures, so that the work surface of these simple laboratory devices can be assigned permanently or also only temporarily to specific workflows. The frame 2 comprises at least one detent rail 6,7, which is arranged on the front or rear frame part 4,5, having detent openings 8,9. Each of these detent openings 8, 9 is implemented and arranged for the insertion and for the sliding guiding of a detent bolt 10, 11 of a tabletop element 3. The sliding direction of the detent bolt is preferably horizontal.

The tabletop elements 3, which are shown transparent here, comprise at least one detent bolt 10,11, which is implemented and arranged for the insertion and for the sliding guiding in one of the detent openings 8,9 of these detent rails 6,7. At least a part of these detent openings 8, 9 is preferably implemented for fixing a corresponding detent bolt 10, 11 of a tabletop element 3 in a vertical direction. The detent rails 6,7 shown here are implemented as laterally open in the area of the detent openings 8,9. The detent openings 8,9 of the detent rails 6,7 are arranged at a regular, modular distance 12. The detent bolts 10,11 of tabletop elements 3 having at least two front or rear detent bolts 10,11 are preferably arranged at the same distance 12 or a multiple of this distance 12.

The tabletop elements 3 can have uniform or differing widths 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 1, tabletop elements 3 are implemented having a width 43 which (viewed from left to right) corresponds to approximately triple, sixfold (6×12), single, single, triple, double, fivefold (5×12), single, and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3. Thus, it is obvious in FIG. 1, for example, that the third tabletop element 3 from the right is equipped with five rear detent bolts 11 and with a row of five front detent bolts 10, the detent bolts 10,11 being arranged four times at equal distance 12 in each of these two rows. Furthermore, it is obvious from FIG. 1 that in the second tabletop element 3 from the right, which is only equipped with one front and one rear detent bolt 10,11, the bolt axis 26 is identical to the plate axis 27. In contrast, in the first tabletop element 3 from the left, which is equipped with three front and three rear detent bolts 10,11, only the middle bolt axis 26 is identical to the plate axis 27.

Figure 2:
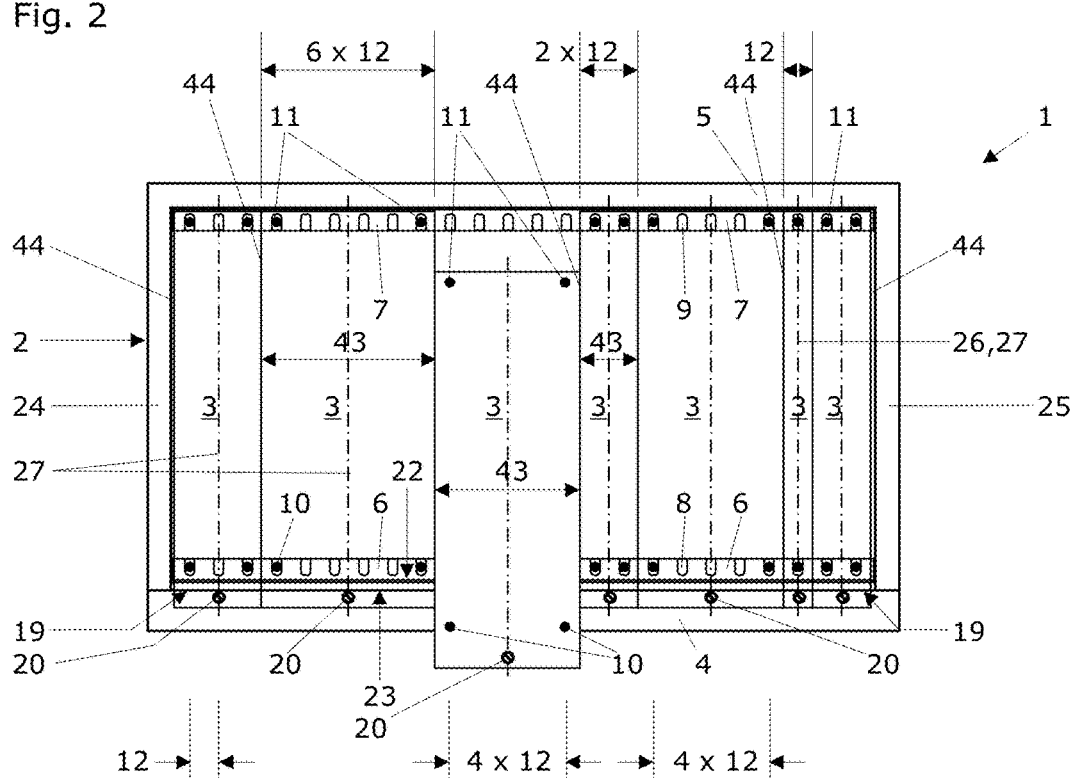
FIG. 2 shows a top view of a laboratory table according to a second embodiment having a number of tabletop elements, which are partially installed in an intermediate space of the frame and partially protrude beyond the frame.

FIG. 2 shows a top view of a laboratory table 1 according to a second embodiment having a number of tabletop elements 3 which are partially installed in an intermediate space of the frame 2 and partially protrude beyond the frame 2. In this second embodiment, all frame parts 4,5 and 24,25 are not actually at the same height as in the first embodiment: The front frame part 4 is somewhat lowered and the installed tabletop elements 3 partially protrude beyond it. Therefore, the frame part 4 is arranged lying lower in relation to the frame part 5 arranged opposite thereto here.

One of the tabletop elements 3, which are shown transparent here, is removed from the frame and in spite of its size, which would offer space for a row of five rear detent bolts 11 and for a row of five front detent bolts 10, only has two front and two rear detent bolts 10,11. However, these four detent bolts 10,11 are arranged so that they correspond to the modular grid of the detent rails 6,7 having the uniform distance 12. The four detent bolts 10,11 are arranged at the points which are as far as possible away from one another; the greatest possible stability of this tabletop element 3 is therefore achieved.

The tabletop elements 3 can have a uniform or differing width 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 2, tabletop elements 3 are implemented having a width 43 which (viewed from left to right) corresponds to approximately triple, sixfold (6×12), fivefold, double (2×12), fivefold, single (12), and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3.

In FIG. 2, all tabletop elements 3 were equipped with at least two, but preferably with four detent bolts 10,11 according to this principle of the greatest possible stability. In the laboratory table 1 shown here, the frame 2 comprises a stop surface 19, which is arranged on the front of the frame parts 4,5 located opposite to one another. This stop surface 19 is implemented here as a vertical upright web on the frame part 4.

All of the tabletop elements 3 shown in FIG. 2 additionally comprise a fixing mechanism 20 arranged on a lower side 21 of the tabletop elements 3. This fixing mechanism 20 is implemented as pivotable around an axis 37 toward the stop surface 19 during the installation of the tabletop elements 3 (cf. FIG. 5A). In the example shown in FIG. 2, the fixing mechanism 20 of the tabletop elements 3 is implemented as a clamping lever 20' (cf. FIG. 10A-10B). This clamping lever 20' comprises a handle 36, a fixing block 35, and a clamping bow 34. The fixing block 35 defines a closure location of the clamping lever 20'. The clamping bow 34 is applied to the stop surface 19 in a springy manner in this closure location of the clamping lever 20' and exerts a spring force on the stop surface 19 (cf. FIG. 10B).

Figure 3:
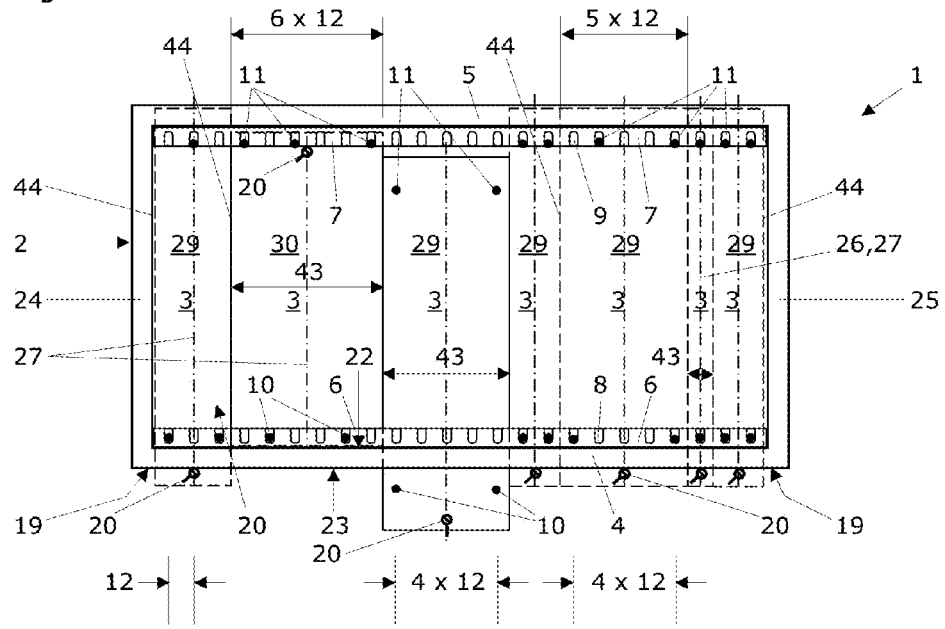
FIG. 3 shows a bottom view of a laboratory table according to a third embodiment having a tabletop element, which is installed in an intermediate space of the frame, of a lower tabletop level and having a number of tabletop elements, which at least partially protrude beyond the frame on both sides, of an upper tabletop level.

FIG. 3 shows a bottom view of a laboratory table 1 according to a third embodiment having a tabletop element 3, which is installed in an intermediate space of the frame 2, of a lower tabletop level 30, and having a number of tabletop elements 3, which at least partially protrude beyond the frame 2 on both sides, of an upper tabletop level 29. In this embodiment shown here, the installed tabletop elements 3 of the upper tabletop level 29 protrude beyond the front frame part 4 and the stop surface 19 on the front frame part 4 (cf. first tabletop element 3 from the left and the four tabletop elements 3 from the right).

This laboratory table 1 comprises at least one frame 2 having a front frame part and a rear frame part 4,5 opposite thereto as well as tabletop elements 3 positionable on this at least one frame 2. The frame 2 comprises at least one detent rail 6,6',7,7', which is positioned on the front or rear frame part 4,5, having detent openings 8,8',9,9'. Each of these detent openings 8,8',9,9' is implemented and arranged for the insertion and for the sliding guiding of a detent bolt 10,11 of a tabletop element 3. The tabletop elements 3 of this laboratory table 1 comprise at least one detent bolt 10,11, which is implemented and arranged for the insertion and for the sliding guiding in one of the detent openings 8,8',9,9' of these detent rails 6,6',7,7'. The sliding direction of the detent bolts 10,11 is preferably horizontal.

In this laboratory table 1, the tabletop elements 3 of the upper tabletop level 29 are only smaller in one horizontal dimension than the frame 2. In contrast, the tabletop elements 3 of the lower tabletop level 30 are smaller in both horizontal dimensions than the frame 2. At least a part, but preferably all of these detent openings 8,8',9,9' are implemented for fixing a detent bolt 10,11 of a tabletop element 3 in a vertical direction. The detent rails 6,6',7,7' are implemented as laterally open in the area of the detent openings 8,8',9,9' here (cf. also FIG. 6A-6C). Notwithstanding this illustration, the detent rails 6,6',7,7' can also be implemented as laterally closed in the area of the detent openings 8,8',9,9' (cf. FIGS. 8A and 8C).

The detent openings 8,9 of the detent rails 6,7 are preferably arranged at a regular distance 12, in a so-called grid. The detent bolts 10,11 of tabletop elements 3 having at least two front or rear detent bolts 10,11 are preferably arranged at the same modular distance 12 or at a multiple of this distance 12. Depending on the provided load of a tabletop element 3, the detent bolts 10,11 (as shown in FIG. 3) can be arranged arbitrarily in position and number and nonetheless following the modular grid dimension defined by the distance 12. The detent rails 6,6',7,7' are preferably fastened on the frame parts 4,5 opposite to one another so that the detent openings 8,8',9,9' of the two detent rails 6,6',7,7' are oriented toward one another.

The tabletop elements 3 can have a uniform or differing width 43 as needed. In any case, however, the tabletop elements 3 have a width 43 which at least approximately corresponds to the regular distance 12 or at least approximately corresponds to a multiple of this distance 12 in the scope of the manufacturing precision. Thus, in FIG. 3, tabletop elements 3 are shown having a width 43 which (viewed from left to right) corresponds to approximately triple, sixfold (6×12), fivefold, double, fivefold (5×12), single, and double the distance 12. To compensate for smaller manufacturing tolerances and allow installation and removal of the individual tabletop elements 3 as desired, narrow joints 44 having a width of a few millimeters can be permitted to form between the installed tabletop elements 3 or between the further frame parts 24,25 and the tabletop elements 3 adjoining thereon. In this manner, a laboratory table 1 can be provided, whose work surface is constructed according to the respective need from greatly varying modules of tabletop elements 3.

Figure 4:
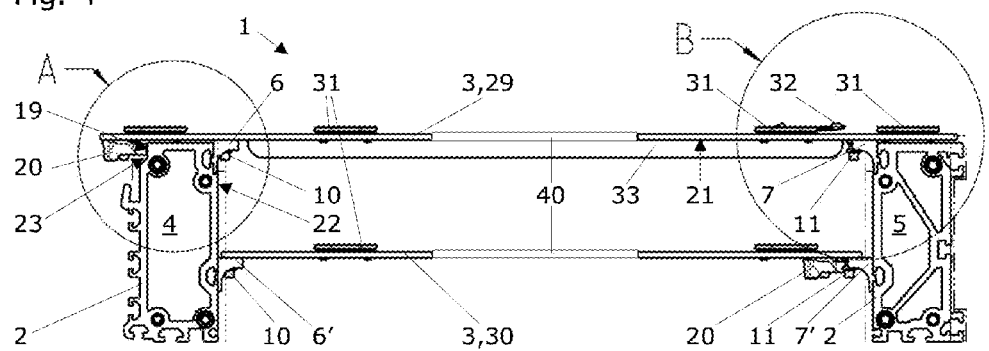
FIG. 4 shows a vertical cross section through the front frame part and the rear frame part of the laboratory table frame having one tabletop element installed in the lower tabletop level and one tabletop element installed in the upper tabletop level.

The laboratory table 1 according to the third embodiment preferably comprises tabletop elements 3 in an upper tabletop level 29 and in a lower tabletop level 30, which are aligned essentially horizontally in the installed state (cf. FIGS. 3 and 4). In addition, the frame parts 4,5 arranged opposite to one another are preferably arranged parallel to one another and the frame 2 preferably comprises two further frame parts 24,25 and is implemented as a rectangular frame. The laboratory table 1 according to the third embodiment can also comprise tabletop elements 3 only in an upper tabletop level 29 or only in a lower tabletop level 30, which are aligned essentially horizontally in the installed state. One tabletop element 3 is preferably arranged either in the upper tabletop level 29 or in the lower tabletop level 30 respectively at one position of the laboratory table 1.

All tabletop elements 3 shown up to this point additionally comprise at least one fixing mechanism 20, which is preferably arranged on a lower side 21 of the tabletop elements 3. This fixing mechanism 20 is implemented as pivotable toward the stop surface 19 around an axis 37 upon installation of the tabletop elements 3. In the example shown in FIG. 3, the fixing mechanism 20 of the tabletop elements 3 is implemented as a clamping lever 20' (cf. FIG. 10A-10B). This clamping lever 20' comprises a handle 36, a fixing block 35, and a clamping bow 34. The fixing block 35 defines a closure location of the clamping lever 20'.

In the tabletop elements 3 of the upper tabletop level 29, the clamping lever 20' is preferably arranged in the front area (close to an operator) of a laboratory table 1, so that the clamping lever 20' can be easily moved manually by the operator. The clamping bow 34 is applied in a springy manner in the closure location of the clamping lever 20' to the stop surface 19 and exerts a spring force on the stop surface 19 (cf. FIG. 10B).

In the tabletop elements 3 of the lower tabletop level 30, the clamping lever 20' is preferably arranged in the rear area (distant from an operator) of the laboratory table 1. Nonetheless (or particularly because of this), the clamping lever 20' can be easily moved manually by the operator. The clamping bow 34 is applied in a springy manner in the closure location of the clamping lever 20' to the detent rail 7' and exerts a spring force on the detent rail 7' (cf. FIG. 11B). Notwithstanding this illustration, in the tabletop elements 3 of the lower tabletop level 30, the clamping lever 20' can be arranged in the front area (close to an operator) of the laboratory table 1. Preferably, only a few tabletop elements 3 are arranged in the lower tabletop level 30, so that as few clamping levers 20' as possible can contribute to a deformation of the frame 2.

In all of the embodiments of the laboratory table 1 according to the present invention shown up to this point, the detent bolts 10,11 are arranged on the lower side 21 of the tabletop elements 3. Notwithstanding this illustration, the detent bolts 10,11 can also be arranged on the upper side of the tabletop elements 3, so that the tabletop elements 3 could be fastened from below on the detent rails 6,6',7,7' (not preferred and not shown).

In all of the embodiments shown up to this point of the laboratory table 1 according to the invention, the detent rails 6,6',7,7' are fastened on the frame parts 4,5 opposite to one another, so that the detent openings 8,8',9,9' of the two detent rails 6,6',7,7' are oriented toward one another. The detent rails 6,6',7,7' are therefore preferably arranged on the table inner side of the frame.

Notwithstanding these illustrations in FIGS. 1 to 3, the detent rails 6,6',7,7' can be fastened on the frame parts 4,5 opposite to another so that the detent openings 8,8',9,9' of the two detent rails 6,6',7,7' are oriented away from one another. The detent rails 6,6',7,7' are then preferably arranged on the table outer side of the frame (not shown). Also notwithstanding these illustrations in FIGS. 1 to 3, the detent rails 6,6',7,7' can also be fastened on the frame parts 4,5 opposite to one another, so that the detent openings 8,8',9,9' of the two detent rails 6,6',7,7' are oriented in the same direction. The detent rails 6,6',7,7' are then preferably arranged either on the table inner side or on the table outer side of the frame (not shown).

FIG. 4 shows a vertical cross section through the front frame part 4 (marked by A) and through the rear frame part 5 (marked by B) of the frame 2 of the laboratory table 1 according to the invention having a tabletop element 3 installed in the lower tabletop level 30 and a tabletop element 3 installed in the upper tabletop level 29 (cf. also FIG. 3). The tabletop elements 3 in the upper tabletop level 29 and/or in the lower tabletop level 30 are preferably aligned essentially horizontally in the installed state.

Cutouts 40 are additionally shown in FIG. 4. One such cutout 40 is applied in a tabletop element 3 arranged at this position of the laboratory table 1, i.e., either in the upper tabletop level 29 or in the lower tabletop level 30. Through this cutout 40, components having taller installation height can be installed on a lower secondary working level in laboratory facilities, so that the movement range of the robots present in these laboratory facilities is impaired substantially less. Alternatively or additionally thereto, such cutouts 40 in tabletop elements 3 of the work surface of laboratory devices or laboratory facilities allow the reaching through or transfer of containers (e.g., for loading/unloading a centrifuge) through the work surface.

As shown in the circle A, the frame 2 comprises a stop surface 19, which is arranged here on the front of the frame parts 4 opposite to one another. This stop surface 19 is an outer surface of the frame part 4 or preferably a milled notch on the frame part 4 here. Very generally, a frame 2 can comprise a stop surface 19, which is arranged on the front or rear of the frame parts 4,5 opposite to one another. In addition, this stop surface 19 can be selected by a person skilled in the art from the group of stop surfaces 19 which comprises an outer surface of a frame part 4,5; a milled notch on a frame part 4,5; a vertical upright web on a frame part 4,5 (cf. FIG. 2), a web protruding horizontally beyond a frame part 4,5, and arbitrary combinations of these stop surfaces 19.

In this exemplary embodiment (cf. also FIG. 3), the installed tabletop elements 3 of the upper tabletop level 29 protrude horizontally beyond the front frame part 4 and the stop surface 19 on the front frame part 4 and the installed tabletop elements 3 of the lower tabletop level 30 laterally approach the frame parts 4,5 arranged opposite to one another. The tabletop elements 3 comprise at least one fixing mechanism 20 arranged on a lower side 21 of the tabletop elements 3, which is implemented as pivotable around an axis 37 toward the stop surface 19 or toward one of the detent rails 6',7' upon installation of the tabletop elements 3.

FIG. 5A-5B shows detail sections of FIG. 4A-4B:

FIG. 5A shows a vertical section through the upper part of the frame 2, i.e., the front frame part 4 having detent rail 6, a stop surface 19, and a tabletop element 3 having clamping lever 20'. This clamping lever 20' is used here as a fixing mechanism 20, which is arranged on a lower side 21 of the tabletop element 3. To fix the installed tabletop element 3, this clamping lever 20' was pivoted around an axis 37 toward the stop surface 19. A clamping bow 34 is thus applied in a closure location, which is defined by a fixing block 35 of the clamping lever 20', in a springy manner to the stop surface 19 and exerts a spring force on the stop surface 19 (cf. FIG. 10B). Through the fixing, the detent bolt 10 is drawn into its end position in the detent rail 6 (cf. FIG. 6C); the frame part 4 having the stop surface 19 is clamped between the combination detent rail 6/detent bolt 10 and the clamping bow 34 of the clamping lever 20'. Blocked fixing of the detent bolt 10,11 thus results. The sliding direction of the detent bolt 10,11 is preferably horizontal.

FIG. 5B shows a vertical section through the upper part of the frame 2, i.e., the rear frame part 5 having detent rail 7 and detent bolt 11. The detent bolt 11 is drawn into its fixed position in the detent rail 7 by the fixing of the tabletop element 3 and fixed therein in relation to movements in the vertical direction (cf. FIG. 6B), in that the holding portions 42 of the detent rail 7 engage in the groove 14 of the detent bolt 11. The displacement of the tabletop element 3 by the fixing results in a distance d between the rear end of the tabletop element 3 and the front edge of a preferably attached vertical rear wall 38.

Reinforcement brackets 33 are preferably provided on the lower side 21 of the tabletop element 3, which increase the stability of the tabletop element 3 and contribute to minimizing the weight of the tabletop element 3. Holding rails 31 are preferably provided on the upper side of the tabletop element 3, which are used for the purpose of exactly positioning arbitrary objects (e.g., so-called "carriers" for microplates, liquid containers, so-called "racks" fur sample tubes, etc.) on the worktable defined by the tabletop elements 3. At least one of these holding rails 31, which fixes the objects in a defined manner in a horizontal x-ray direction, preferably comprises a detent cam 32, which also fixes this object in the horizontal Y direction extending perpendicularly thereto in a defined manner.

FIG. 6A-6C shows detail views of a detent rail/detent bolt combination according to a first embodiment variant, which is characterized in that the detent rails 6,6',7,7' are implemented as laterally open in the area of the detent openings 8,8',9,9', a holding web 13 is arranged in the detent openings 8,8',9,9' of the detent rails 6,6',7,7', and the detent bolts 10,11 have a circular cross section and comprise a peripheral groove 14, whose width is adapted to the height of the first holding web 13 in the detent openings 8,8',9,9' of the detent rails 6,6',7,7'.

Notwithstanding this definition, the detent bolts 10,11 can also have a shape which deviates from the preferred cylindrical shape. The detent bolts can thus, for example, have an oval, elliptical, or polygonal cross section (with or without rounded corners). In addition, the groove 14 does not have to be implemented as peripheral. The groove 14 can also only be located on those sides of the detent bolts 10,11 which extend parallel to the guide direction (Y direction) of the holding webs 13, which also only extend in the Y direction.

As a further alternative embodiment of the detent bolts 10,11, it can be provided that the detent bolts 10,11 have a continuously uniform cross section (not shown) and therefore can be designated as a "pin". Such "pins" do not provide any hold of the tabletop elements 3 in the vertical Z direction, however, because they also do not engage below possibly provided first or second holding webs 13,13'. However, it can be entirely sufficient for the stability of the tabletop to only provide a pin and no detent bolt 10,11 on the side of a tabletop element 3 on which the clamping mechanism 20 is arranged; in such a case, a detent bolt 10,11 would only be provided on the side of the tabletop element 3 opposite to the fixing mechanism 20, because on one side the clamping using the fixing mechanism 20 can already cause sufficient securing for the tabletop elements 3. This is the case above all if no objects (e.g., pipette tips or microplates)

must be received by these tabletop elements 3 against the resistance of a holding mechanism arranged on these tabletop elements 3 or against another resistance. If only "pins" are used as the detent bolts 10,11, the arrangement of holding webs 13,13' can be omitted; however (to improve the adhesion of the tabletop elements 3 on the frame 2), it can be provided that a fixing mechanism 20 is arranged in each case on both sides of the tabletop element 3. As shown, depending on the need and the given conditions, the provision of an arbitrary combination and number of detent bolts 10,11 and/or "pins" and fixing mechanisms 20 is possible.

FIG. 6A shows the detent bolt 11 upon countersinking in the rear upper detent rail 7 during the installation of the tabletop element 3. The tabletop element 3 preferably protrudes beyond the rear frame part 5 and more preferably touches the front side of a rear wall 38. This detent bolt 11 (having the bolt axis 26) plunges into a recess 15 in the detent opening 9, the diameter of the recess 15 being somewhat larger than the largest cross section 16 of the detent bolt 11. Infeed chamfers on both flanks of the detent opening 9 make it easier to center and therefore insert the detent bolt 11 into the recess 15. The letters A-A identify the section line of the illustration in FIG. 7A. The holding portions 42 of the first holding web 13 are well visible here and are not concealed by the detent bolt 11.

FIG. 6B shows the detent bolt 11 in a fixing position in the rear upper detent rail 7, the detent bolt 11 (having the bolt axis 26) being fixed in this fixing position in the horizontal X direction so that it is fixed in the Z direction. This is preferably produced in that the holding webs 13 in the detent openings 9 of the detent rail 7 are implemented as open on one side in the horizontal direction, and the holding webs 13 in the detent openings 9 of the detent rails 7 for vertically fixing and horizontally guiding the detent bolt 11 each have a constriction 18 on their open side, which is wider than a reduced cross section 17 of the detent bolt 11 in the area of the groove 14, but is narrower than the largest cross section 16 of the detent bolt 11. Through the holding portions 42 (shown by dashed lines here, because they are largely concealed by the detent bolt 11), which are arranged on the constriction 18, of the holding webs 13, which engage in the groove 14 of the detent bolt 11, this detent bolt 11 is prevented from moving in the Z direction. The letters B-B identify the section line of the illustration in FIG. 7B. The detent bolt 11 is simultaneously guided in the horizontal direction by the two holding portions 42 spaced apart by the constriction 18 (cf. FIG. 6C). The two holding portions 42 practically touch the base of the groove 14 in the detent bolt 11 and guide it in the horizontal direction, so that this detent bolt 11 cannot deviate in the longitudinal direction of the rear frame part 5.

FIG. 6C shows the detent bolt 10 in an end position, in which it is fixed blocked in the front upper detent rail 6. In this position of the detent bolt 10, the holding web 13 in the detent opening 8 of the detent rail 6 engages in the groove 14 in the detent bolt 11 and fixes it in the vertical direction and parallel to the longitudinal direction of the front frame part 4. The detent openings 8 of the detent rail 6 each have a constriction 18 on their open side for vertically fixing and horizontally guiding the detent bolt 11. If the detent bolt 10 has a rectangular cross section, notwithstanding the illustrations in FIG. 6A-6C, for example, and only comprises a groove 14 on the two sides which extend parallel to the guide direction (Y direction) of holding webs 13 also only extending in the Y direction, the detent bolt 11 is located in its end position having one side on the detent rail 6 which does not have a groove 14. Correspondingly, the detent rail 6 also could not have a holding web 13 at this point of the detent opening 8. The letters C-C identify the section line of the illustration in FIG. 7C. The holding portions 42 of the first holding web 13 are well visible here and are not concealed by the detent bolt 11.

FIG. 7A-7C shows detail sections through the detent rail/detent bolt combination according to the first embodiment variant of FIG. 6A-6C. As shown, the detent bolt 11 is preferably implemented as cylindrical, this allows more cost-effective manufacturing. The detent bolt 11 preferably has, on its rear end, a cylindrical constriction, using which it is fastened in a correspondingly dimensioned hole of the tabletop element 3. Preferred fastenings of the detent bolts 10,11 in the tabletop elements 3 comprise, for example, the use of a press fit and/or adhesives.

FIG. 7A shows the detent bolt 11 (having the bolt axis 26) placed in the recess 15 of the detent rail 7 during the installation of the tabletop element 3. The largest cross section 16 of this detent bolt 11 is, of course, smaller than the diameter of the recess 15, which is free of holding webs 13, which could engage in the groove 14 of the detent bolt 11. The letters A-A identify the section line of the illustration in FIG. 9A.

FIG. 7B shows the detent opening 9 behind the detent bolt 11. It is clear here that the recess 15 does not have holding webs 13. Holding webs 13 are therefore only shown in the horizontal projection here, but not in section. The detent rail 7 preferably has infeed chamfers 28, which make it easier to correctly position the detent bolt 11 in the detent opening 9 of the detent rail 7. The letters B-B identify the section line of the illustration in FIG. 9B.

FIG. 7C shows the detent bolt 10 in an end position, in which it is fixed blocked in the front upper detent rail 6. It is clear here that the holding webs 13 engage in the groove 14 of the detent bolt 10, but the reduced cross section 17 of the detent bolt 10 is somewhat smaller than the opening of the oblong hole 15' between the holding webs 13. The letters C-C identify the section line of the illustration in FIG. 9C.

FIG. 8A-8C shows detail views of a detent rail/detent bolt combination according to a second and third embodiment variant. The second and third embodiment variants also differ from the first embodiment variant, inter alia, in that the first holding web 13 (according to the first embodiment variant) is relatively narrow and engages in a groove 14 on a detent bolt 10,11, which essentially has the cross-sectional shape of a "recumbent H". In contrast, the detent bolt 10,11 in the second and third embodiment variants has a cross-sectional shape which essentially corresponds to an "upside-down T".

The second embodiment variant is characterized in that the detent rails 6,6',7,7' are implemented as laterally closed in the area of the detent openings 8,8',9,9', a second holding web 13' is arranged in the detent openings 8,8',9,9' of the detent rails 6,6',7,7', and the detent bolts 10,11 have a circular cross section and comprise a reduced cross section 17, whose width is adapted to the height of the second holding web 13' in the detent openings 8,8',9,9' of the detent rails 6,6',7,7'. As shown, the second embodiment variant of the detent rails 6,6',7,7' comprises a recess 15, which is arranged approximately in the middle of the detent openings 8,8',9,9'.

The third embodiment variant is characterized in that the detent rails 6,6',7,7' are implemented as laterally open in the area of the detent openings 8,8',9,9', a second holding web 13' is arranged in the detent openings 8,8',9,9' of the detent rails 6,6',7,7', and the detent bolts 10, 11 have a circular cross section and comprise a reduced cross section 17, whose width is adapted to the height of the second holding web 13' in the detent openings 8,8',9,9' of the detent rails 6,6',7,7'. As shown, in comparison to the second embodiment variant, the third embodiment variant of the detent rails 6,6',7,7' does not comprise a recess 15.

FIG. 8A shows the detent bolt 11 (having the bolt axis 26) upon countersinking in the rear upper detent rail 7 according to a second embodiment variant during the installation of the tabletop element 3. The tabletop element 3 preferably protrudes beyond the rear frame part 9 and more preferably touches the front side of a rear wall 38. The largest cross section 16 of this detent bolt 11 is, of course, smaller than the diameter of the recess 15, which is free of holding webs 13', which could engage in the reduced cross section 17 of the detent bolt 11. The detent rail 7 preferably has infeed chamfers 28, which make it easier to correctly position the detent bolt 11 in the detent opening 9 of the detent rail 7 of the second embodiment variant.

FIG. 8B shows the detent bolt 11 (having the bolt axis 26) upon insertion into the rear upper detent rail 7 of the third embodiment variant during the installation of the tabletop element 3.

FIG. 8C shows the detent bolt 10 (having the bolt axis 26) in an end position, in which it is fixed blocked in the front upper detent rail 6 of the second embodiment variant.

FIG. 9A-9C shows detail sections through the detent rail/detent bolt interaction according to the second and third embodiment variants of FIG. 8A-8C.

FIG. 9A shows the detent bolt 11 (having the bolt axis 26) placed in the recess 15 of the detent rail 7 during the installation of the tabletop element 3. The largest cross section 16 of this detent bolt 11 is, of course, smaller than the diameter of the recess 15, which is free of holding webs 13', which could engage in the reduced cross section 17 of the detent bolt 11.

FIG. 9B shows the detent opening 9 behind the detent bolt 11. The detent rail 7 preferably has infeed chamfers 28, which make it easier to correctly position the detent bolt 11 in the detent opening 9 of the detent rail 7.

FIG. 9C shows the detent bolt 10 in an end position, in which it is fixed blocked in the front upper detent rail 6. It is clear here that the holding webs 13' engage in the reduced cross section 17 of the detent bolt 10, but the reduced cross section 17 of the detent bolt 10 is somewhat smaller than the opening of the oblong hole 15' between the holding webs 13'.

FIG. 10A-10B shows detail views of a clamping lever/stop surface interaction in the upper tabletop level 29 of a laboratory table 1, which comprises at least one frame 2 having a front frame part and a rear frame part 4,5 opposite thereto as well as tabletop elements 3 positionable on this at least one frame 2. The frame 2 comprises a stop surface 19, which is arranged here on the front of the frame parts 4 opposite to one another and is implemented here as a web standing vertically upright beyond the frame part 4. The tabletop element 3 comprises at least one fixing mechanism 20 arranged on its lower side 21, which is implemented as pivotable around an axis 37 toward the stop surface 19 during the installation of the tabletop element 3. This fixing mechanism 20 is shown in FIG. 10A as a clamping lever 20' in the open position.

The at least one fixing mechanism 20 of the tabletop element 3 is implemented here as a clamping lever 20'. This clamping lever 20' comprises a handle 36, a fixing block 35, and a clamping bow 34. The fixing block 35 defines a closure location of the clamping lever 20' in a locked position (cf. FIG. 10B). The clamping bow 34 is applied in a springy manner to the stop surface 19 in this closure location of the clamping lever 20' and exerts a spring force on the stop surface 19.

One practical detail is additionally obvious in FIG. 10A-10B: If the clamping lever 20' is not located in the locking position, the handle 36 preferably protrudes visibly beyond the front edge of the tabletop element 3 (cf. FIG. 10A). The handle 36 preferably only disappears below the front edge of the tabletop element 3 when the clamping lever 20' is located in the locked position (cf. FIG. 10B). A simple visual check provides information in this case about whether all tabletop elements 3 have been fixed and locked as prescribed. This arrangement is particularly preferable for the tabletop elements 3 which are arranged in an upper tabletop level 29 (cf. FIGS. 4 and 5A-5B).

A further practical detail relates to the so-called overtightening guard 41 in tabletop elements 3 in the upper tabletop level 29: A bolt is arranged on the lower side 21 of the corresponding tabletop element 3 so that the handle 36 of the clamping lever 20' assumes an end position upon disengagement of the fixing mechanism 20. This end position is selected so that the handle 36 cannot be pivoted too far unintentionally and disappears under the front edge of the tabletop element 3. Such a disappearance could incorrectly be misinterpreted as an indication that the clamping lever 20' is located in the locking position.

FIG. 11A-11B shows detail views of a clamping lever/detent rail interaction in the lower tabletop level 30 of a laboratory table 1 according to the invention, which comprises at least one frame 2 having a front frame part and a rear frame part 4,5 opposite thereto, as well as tabletop elements 3 positionable on this at least one frame 2.

The frame 2 has detent rails 6,6',7,7' having detent openings 8,8',9,9'. A lower rear detent rail 7', which is arranged on the rear of the frame parts 5 opposite to one another, is shown here.

The tabletop element 3 comprises at least one fixing mechanism 20 arranged on its lower side 21, which is implemented as pivotable around an axis 37 toward the detent rail 7' upon installation of the tabletop element 3. This fixing mechanism 20 is shown in FIG. 11A as a clamping lever 20' in the open position.

The at least one fixing mechanism 20 of the tabletop element 3 is implemented here as a clamping lever 20'. This clamping lever 20' comprises a handle 36, a fixing block 35, and a clamping bow 34. The fixing block 35 defines a closure location of the clamping lever 20' in a locked position (cf. FIG. 11B). The clamping bow 34 is applied in a springy manner to the detent rail 7' in this closure location of the clamping lever 20' and exerts a spring force on the detent rail 7'.

FIG. 12A-12F shows detail sections through a rear upper detent rail 7 during the installation of a tabletop element 3 in the frame 2 of a laboratory table 1 according to the invention. The method carried out in this case for providing a laboratory table 1, which comprises at least one frame 2 having a front frame part and a rear frame part 4,5 opposite thereto as well as tabletop elements 3 positionable on this at least one frame 2, is characterized in that the frame 2 comprises at least one detent rail 6,6',7,7', which is arranged on the front or rear frame part 4,5, having detent openings 8,8',9,9'. Each of these detent openings 8,8',9,9' is implemented and arranged for the insertion and for the sliding guiding of a detent bolt 10,11 of a tabletop element 3. In this method, the tabletop elements 3 are installed using at least one detent bolt 10,11 in this frame 2, in that the at least one detent bolt 10,11 is inserted into one of the detent openings 8,8',9,9' of these detent rails 6,6',7,7' and guided in a sliding manner therein. The sliding direction of the detent bolt 10,11 is preferably horizontal and perpendicular to the longitudinal direction of the rear frame part 5.

FIG. 12A shows the first step of inlaying a tabletop element 3 with application to the rear detent rail 7, which is used as the guide means for reaching the pivot position. The diagonally held tabletop element 3 having the detent bolt 11 fastened captive thereon and its bolt axis 26 are well visible. The upper rear detent opening 9 (having recess axis 39 and infeed chamfers 28) of the upper rear detent rail 7 is also visible, which is ready to receive the detent bolt 11. The detent bolt 11 shown here corresponds to a first embodiment, in which it is immovably fixed by means of a press fit in a corresponding opening in the tabletop element 3.

FIG. 12B shows the second step of inlaying the tabletop element 3 with additional application to a rear stop, this rear stop being able to be provided by a part of the frame 2 or also by the front side of a rear wall 38. The individual parts are the same as in FIG. 12A. In addition, the recess 15 in the detent opening 9 of the detent rail 7 is well visible here. This recess 15 has a cross section which is larger than a largest cross section 16 of the detent bolts 10, 11 (cf. FIGS. 12C and 12E).

FIG. 12C shows the third step of inlaying the tabletop element 3 with pivoting into the horizontal while simultaneously applying it to the rear detent rail 7 and the rear stop. It may be seen well that the bolt axis 26 and the recess axis 39 assume an identical position through this pivoting, as soon as the detent bolt 11 plunges completely into the recess 15. In addition, the recess 15, into which the detent bolt 11 is about to plunge, is marked here. This recess 15 has a cross section which is larger than the largest cross section 16 of this detent bolt 11.

FIG. 12D shows the fourth step of inlaying the tabletop element 3 with horizontal displacement and fixing of the tabletop element 3. This horizontal displacement is performed by the locking of the fixing mechanism 20, which can have many formations and can be implemented, e.g., as an eccentric, clamping lever, snap lever, slide, and the like. However, the clamping lever 20' shown in FIGS. 10A-10B and 11A-11B is preferred. The detent bolt 11 shown here corresponds to the first embodiment as in preceding FIGS. 12B and 12C, in which it is immovably fixed in a corresponding opening in the tabletop element 3 by means of a press fit.

FIG. 12E shows the third step of inlaying the tabletop element 3 with pivoting into the horizontal while simultaneously applying a detent bolt 11 to the rear detent rail 7 and the rear stop. The detent bolt 11 shown here corresponds to a second embodiment, in which it is fixed so it is rotatable around the bolt axis 26 in a corresponding opening in the tabletop element 3 by means of a countersunk, soldered, or spotwelded disc. In addition, the recess 15 into which the detent bolt 11 is about to plunge is marked here. This recess 15 has a cross section which is larger than the largest cross section 16 of this detent bolt 11.

FIG. 12F shows the fourth step of inlaying the tabletop element with horizontal displacement and fixing of the tabletop element using a detent bolt according to a third embodiment. The detent bolt 11 shown here corresponds to a third embodiment, in which it is fixed so it is rotatable around the bolt axis 26 in a corresponding opening in the tabletop element 3 by means of a clip ring.

The detent bolts 10,11 are particularly preferably implemented as captive and are connected fixed in place to the respective tabletop element 3. Therefore, each detent bolt 10,11 can be fixed individually on the tabletop element 3, in that it is fixed immovably, e.g., by means of a press fit and/or by means of application of adhesives, welding, and/or soldering, at a specific location of a tabletop element 3. Alternatively, the detent bolts 10,11 can also be implemented as rotatable around their bolt axis 26 and nonetheless can be connected fixed in place to the tabletop element 3, which can also be achieved by riveting the detent bolts 10,11 to the tabletop elements 3, for example.

The at least one clamping lever 20' of the tabletop elements 3 is preferably arranged on a lower side 21 of the tabletop elements 3 and arranged so it is pivotable toward a table inner side 22 or toward a table outer side 23 of the stop surface 19. Arbitrary other arrangements of the clamping lever 20' in conjunction with the practically arbitrary arrangement of the detent rails 6,6',7,7' and detent openings 8,8',9,9' will be selected by a person skilled in the art depending on the situation and the tabletop elements 3 will thus be fastened on the frame 2 by means of spreading or blocking. Depending on the type of fastening, the attachment of a spring to those detent bolts 10, 11 and/or detent rails 6,6',7,7' which are arranged on the side opposite to the fixing mechanism 20 of a tabletop element 3 (but also on the lower side 21) is recommended.

As shown, each tabletop element 3 comprises at least one fixing mechanism 20 spaced apart from the detent bolt, which fixes the tabletop element 3 in a locking position and holds the detent bolts 10,11, which are guided parallel to a tabletop axis 27 of the tabletop element 3 (cf. FIGS. 1-3 and FIG. 11A-11B), in the detent rail 6,7 in a fixing position. The detent bolt 10,11 is preferably guided in a sliding manner in the detent rail 6,7 if the detent bolt 10,11 is fixed immovably in the tabletop element 3. If the detent bolt 10,11 is fixed so it is rotatable in the tabletop element 3, it is preferably guided in a sliding and/or rolling manner. At least a part of the detent openings 8,8',9,9' is preferably implemented to fix a detent bolt 10,11 of a tabletop element 3 in a vertical direction, the detent bolts 10,11 being guided in a horizontal direction and being fixed in the vertical direction in the locking position of the tabletop element 3 in the detent openings 8,8',9,9' of the detent rails 6,6',7,7'.

A method for installing a tabletop element 3 preferably comprises the following steps:
a) applying an edge of the tabletop element 3 to a detent rail 6',7 or a frame part 5;
b) applying an edge of the tabletop element 3 to a stop, the stop being provided by frame part 4 or by a rear wall 38;
c) pivoting the tabletop element 3 in the horizontal while simultaneously applying it to the stop and the detent rail 6',7 or the frame part 5; and
d) horizontally displacing and fixing the tabletop element 3 using the fixing mechanism 20.

In the above-described method, a clamping lever 20' is preferably used as the fixing mechanism 20, the clamping lever 20' preferably being arranged on a lower side of the tabletop elements 3 and being pivoted toward a stop surface 19 or toward one of the lower detent rails 6',7' around an axis 37 during the installation of the tabletop elements 3. A clamping bow 34 is applied in a springy manner to the stop surface 19 or the detent rail 6',7' and exerts a spring force on the stop surface 19 or the detent rail 6', 7' in a closure location defined by a fixing block 35 of the clamping lever 20'. A method for replacing a tabletop element 3 preferably comprises the following steps, which are executed before installing another tabletop element 3:

a) disengaging the fixing mechanism 20 and horizontally displacing the tabletop element 3 until it is applied to the stop and the detent rail 6',7 or the frame part 5;
b) pivoting the tabletop element 3 out of the horizontal while simultaneously applying it to the stop and the detent rail 6',7 or the frame part 5; and
c) lifting up the tabletop element 3.

Additional embodiments of detent bolts and fixing mechanisms of the laboratory table 1 according to the present invention are now described with the aid of the FIGS. 13A-13B to 21A-21B, but without limiting the scope of the claims.

According to the present invention, a first type of a laboratory table 1 comprises a front frame part 4 and a rear frame part 5 opposite thereto and further comprises replaceable tabletop elements positionable on these front and rear frame parts 4,5. This first type of an inventive laboratory table 1 comprises a number of detent openings 8,8',9,9' arranged at a regular distance 12 on the front frame part 4 and/or on the rear frame part 5. This regular distance 12 defines a modular grid. Each one of these detent openings 8,8',9,9' is implemented and arranged for insertion of a detent bolt 10,11 of a replaceable tabletop element 3 positioned on these front and rear frame parts 4,5. In this first type of an inventive laboratory table 1, each replaceable tabletop element 3 is configured as a modular tabletop element 3 which comprises at least two detent bolts 10,11 that are implemented and arranged for the insertion into one of the detent openings 8,8',9,9' of the laboratory table 1.

Though not imperative, it is particularly preferred that each one of these detent openings 8,8',9,9' is also implemented and arranged for sliding guiding of a detent bolt 10,11 of a replaceable tabletop element 3 positioned on these front and rear frame parts 4,5. This preference applies to all sorts of detent bolts 10,11 whether they are implemented as e.g. pins, screws, noses, projections, or slides and whether they are orientated vertically or horizontally or slightly deviating from horizontal or vertical orientation.

In this first type of an inventive laboratory table 1, it is preferred that each replaceable tabletop element 3 has a width 43 which at least approximately corresponds to the regular distance 12 or at least approximately corresponds to a multiple of this regular distance 12. It is further preferred that detent bolts 10,11 of the replaceable tabletop elements 3 with a width 43 that at least approximately corresponds to a multiple of this regular distance 12 are arranged following the modular grid dimension defined by the distance 12.

Preferably, a modular tabletop element 3 has a width 43 that not exactly corresponds to the regular distance 12 or not exactly corresponds to a multiple of this regular distance 12. For ease of insertion and removal of such a tabletop element 3, it is preferred that a small gap exists between two modular tabletop elements 3 when mounted on the inventive laboratory table 1. In any case however, the mutual arrangement of detent openings 8,8',9,9' and detent bolts 10,11 according to the modular grid as defined by the regular distance 12 provides for exact positioning of the replaceable tabletop elements 3 on the front and rear frame parts 4,5 of the laboratory table 1. If required, masking or seals can be applied to the gaps between the modular tabletop elements 3.

Preferably, the detent bolts 10,11 are implemented as captive and are immovably connected fixed in place to the respective tabletop element 3 (see also FIGS. 13A-13B to 19A-19B). In a preferred alternative, the detent bolts 10,11 are implemented as rotatable around a bolt axis 26 and are connected fixed in place to the replaceable tabletop element 3 (see also FIG. 15A-15B).

Preferably, the detent bolts 10,11 of replaceable tabletop elements 3 having at least two front detent bolts 10 or having at least two rear detent bolts 11 are arranged at the same regular distance 12 or in a multiple of this regular distance 12 (see FIGS. 1 and 2).

Preferably, the detent bolts 10,11 have a cylindrical shape having continuously identical cross section (see also FIG. 21A-21B). Preferably, each replaceable tabletop element 3 comprises on a lower side 21 at least one fixing mechanism 20 on one or both sides of the tabletop element 3 and spaced apart from the detent bolts 10,11, which fixing mechanism 20 fixes the tabletop element 3 in a locking position (see also FIGS. 14A-14B to 19A-19B, and 21A-21B).

Preferably, the at least one fixing mechanism 20 is implemented as pivotable around an axis 37 toward a stop surface 19 or toward a detent rail or detent element 6',7' at one or both of the and rear frame parts 4,5 during the installation of the replaceable tabletop elements 3. It is further preferred that the at least one fixing mechanism 20 of the replaceable tabletop elements 3 is implemented as a clamping lever 20', this clamping lever 20' comprising a handle 36, a fixing block 35, and a clamping bow 34, the fixing block 35 defining a closure location of the clamping lever 20', and the clamping bow 34, in this closure location of the clamping lever 20', being applied in a springy manner to the stop surface 19, or to the detent rails or detent elements 6',7' and exerting a spring force on the stop surface 19 or on the detent rails or detent elements 6',7' (see FIGS. 10A-10B and 11A-11B)

Preferably, at least some of the detent bolts 10,11 have a circular cross section and comprise a groove 14, whose width is adapted to a height of a first holding web 13 in the detent openings 8,8',9,9' of detent rails or detent elements 6,6',7,7' that are arranged at the front or rear frame part 4,5; the detent openings 8,9 of the detent rails or detent elements 6,7 being arranged at a regular, modular distance 12 (see FIGS. 6A-6C to 8A-8C). It is further preferred that at least a part of these detent openings 8,9 is implemented for fixing a corresponding detent bolt 10,11 of a replaceable tabletop element 3 in a vertical direction. Preferably, to those detent bolts 10,11 and/or detent rails or detent elements 6,6',7,7' which are arranged on the side opposite to the fixing mechanism 20 of a replaceable tabletop element 3 a spring is attached. Preferably, the detent bolts 10,11 fixed in the vertical direction in the detent openings 8,8',9,9' of the detent rails or detent elements 6,6',7,7' in a locking position of the replaceable tabletop element 3, are guided in a horizontal direction.

Generally, when speaking about detent rails and detent elements 6,6',7,7' and as apparent from the above description of a preferred laboratory table 1, the expression "detent element" is a synonym to the previously utilized expression "detent rail". Both, "detent elements" and "detent rails", preferably are linearly arranged on one or both frame parts 4,5 of a preferred laboratory table 1. However, a "detent element" can be very compact and only comprising a single "detent opening". More extended "detent elements" may comprise two or more "detent openings" that still are linearly arranged on one or both frame parts 4,5. Extended "detent elements" that contain more than two "detent openings" preferably are called "detent rails".

As further apparent from the above description of a preferred laboratory table 1, the expression "detent extension" is a synonym to the previously utilized expression "detent bolt". Both, "detent extensions" and "detent bolts", preferably are linearly arranged on one or both frame parts 4,5 of a preferred laboratory table 1.

Deviating from the embodiments as shown in the Figures, a frame part for supporting detent elements 6,7 or detent extensions 10,11 can be configured as an intermediate frame part that is located between the front and rear frame parts 4,5. It is however still preferred that the detent elements 6,7 or detent extensions 10,11 of the intermediate frame part can be brought into a mutual fixing position with the corresponding detent elements 6,7 or detent extensions 10,11 of a replaceable tabletop element 3, and that the corresponding detent elements 6,7 or detent extensions 10,11 of a replaceable tabletop element 3 still are spaced apart from the at least one fixing mechanism 20.

As below described however, the fixing mechanism can be incorporated in the detent elements 6,7 or detent extensions 10,11. It is thus preferred that the laboratory table 1 comprises fixing mechanisms 20 that are configured for fixing the replaceable tabletop elements 3 positioned on these front and rear frame parts 4,5 in a locking position, said fixing mechanisms 20 being:

- attached to or integrated in a replaceable tabletop element 3, or
- attached to or integrated in a detent bolt 10,11, or
- attached to or integrated in a detent rail or detent element 6,6',7,7', or
- attached to or integrated in a front frame part 4 or rear frame part 5.

Preferably, the laboratory table 1 comprises replaceable tabletop elements 3 in an upper tabletop level 29 and/or in a lower tabletop level 30, all replaceable tabletop elements 3 being aligned essentially horizontally in the installed state.

Preferably, the frame parts 4,5 arranged opposite to one another are arranged parallel to one another, and the frame 2 comprises two further frame parts 24,25 and is implemented as a rectangular frame.

FIG. 13A-13B shows vertical section and top views of first and second additional embodiments of detent bolts 10,11 and fixing mechanisms 20.

FIG. 13A is showing a detent bolt 10 that comprises a fixing mechanism 20 configured as a flip part 45. In particular, it is shown that a front detent bolt 10 (it could also be a rear detent bolt 11) has a bolt axis 26 extending perpendicular to the replaceable tabletop element 3. The front detent bolt 10 (or rear detent bolt 11) comprises a fixing mechanism 20 configured as a flip part 45 that is mounted to the detent bolt 10 and that is tiltable about an axis 46. The front detent bolt 10 (or rear detent bolt 11) all over has a substantially continuous cross section when the flip part 45 is being hold in an insert position for positioning on or removing a tabletop element 3 from these front and rear frame parts 4,5. Thus, the detent bolts 10,11 are configured for insertion into holes 52 of a support bar 53 (shown in FIG. 13A) or of the front and rear frame parts 4,5 (not shown).

In a variant, the flip part 45 that is mounted to the detent bolt 10,11 and that is tiltable about an axis 46 may have a shape deviating from a cylinder-part, e.g. having a trapezoid form. Accordingly, the axis 46 may be located close to a narrow end of the flip part 45, which supports ease insertion of the detent bolt 10,11 and its flip part 45 into a hole 52 of a support bar 53.

Preferably in the insert position, the flip part 45 is biased with respect to the front or rear detent bolt 10,11 by a spring 59, preferably in the form of a spiral spring 59. Such biasing causing the flip part 45 to flip about its axis 46 into a locking position in which the flip part 45 protrudes beyond the substantially continuous cross section of the front detent bolt 10 or rear detent bolt 11. The axis 46 may be positioned eccentric (as shown in FIG. 13A) or centric with respect to the bolt axis 26.

Preferably for removing a particular tabletop element 3, the flip part 45 is configured to be hold in the insert position manually or by a guide 47 that may be positioned below the replaceable tabletop element 3. The guide 47 may be lifted up and placed around the detent bolt 10,11 so that the flip part 45 is brought in line with the shape of the detent bolt 10,11.

Alternatively, the flip part 45 is mounted tiltable about an eccentric axis 46 and comprises magnetizable material. Gravity of the flip part 45 causing the flip part 45 to flip about its eccentric axis 46 into a locking position, in which the flip part 45 protrudes beyond the substantially continuous cross section of the front or rear detent bolt 10,11. In this case, the flip part 45 preferably is configured to be hold in the insert position manually, by a guide 47, or by a magnet 48. The magnet 48 preferably is positioned on the replaceable tabletop element 3 to attract the flip part 45 in order to bring it in line with the shape of the detent bolt 10,11.

Indicated in the top view of FIG. 13A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown).

In consequence, a combination of such a detent bolt 10,11 with a hole 52 in the support bar 53 is also configured as a fixing mechanism 20 that fixes the tabletop element 3 against horizontal or vertical movements.

FIG. 13B is showing a detent bolt 11 that comprises a turned down portion 69 which is implemented to be acted on by at least one spring 59. In particular, it is shown that a rear detent bolt 11 (it could also be a front detent bolt 10) has a bolt axis 26 extending perpendicular to the replaceable tabletop element 3. This rear detent bolt 11 is implemented for insertion into a hole 52 of a support bar 53 (shown) or of the front or rear frame parts 4,5 (not shown) of the laboratory table 1. This rear detent bolt 11 comprises a turned down portion 69 that is implemented to be acted on by at least one spring 59. This at least one spring 59 is attached to the laboratory table 1. In the FIG. 13B, this at least one spring 59 is attached to a support bar 53. Preferably, such a front or rear detent bolt 10,11 has a cylindrical shape comprising the turned down portion 69. Preferably, the spring 59 is equipped with a ring or handle 60, with which the spring can be disengaged from the turned down portion 69 of the detent bolts 10,11 (see double arrow in FIG. 13B) for ease of removing the replaceable tabletop element 3 from the laboratory table 1.

Deviating from a cylindrical shape, such a front or rear detent bolt 10,11 that comprises a turned down portion 69 may have a cross section that is not circular, but square, rectangular, regularly or irregularly polygonal, or any combination of these.

In consequence, a combination of such a detent bolt 10,11 with a hole 52 in the support bar 53 and at least one spring 59 attached to the support bar 53 is also configured as a fixing mechanism 20 that fixes the tabletop element 3 against horizontal or vertical movements.

The first and second additional embodiments of detent bolts 10,11 and fixing mechanisms 20 allow vertically inserting the detent bolts 10,11 in the holes 52 of the support bars 53. Also fixing the tabletop elements 3 in this insert position is provided by the fixing mechanisms 20 disclosed in FIG. 13A-13B. In consequence, horizontal movement of the tabletop elements 3 is not necessary and practically the entire area between the front and rear frame parts 4,5 may be covered by the tabletop elements 3. Thus, only a small gap may be left between the front and rear frame parts 4,5 and the tabletop elements 3.

FIG. 14A-14B shows vertical section and top views of third and fourth additional embodiments of detent bolts and fixing mechanisms.

FIG. 14A is showing a detent bolt positioned below the replaceable tabletop element and comprising magnetizable material or a magnet. In particular, it is shown that a front detent bolt 10 (it may also be a rear detent bolt 11) is positioned below the replaceable tabletop element 3. The detent bolt 10 has a bolt axis 26 that extends perpendicular to the tabletop element 3. The front detent bolt 10 comprises magnetizable material 51 (shown) or a magnet 48 (not shown) and is configured to be positioned in a hole 52 of a support bar 53 that comprises magnetizable material 51 (not shown) or a magnet 48 (shown). Preferably, the magnet 48 comprised by the support bar 53 of the laboratory table 1 is selected from a group comprising permanent magnets, electromagnets, and switchable permanent magnets (all of them being known per se in the prior art). In consequence, such a combination of a detent bolt 10,11 with a magnet 48 is also configured as a fixing mechanism 20 that fixes the tabletop element 3 against horizontal or vertical movements.

As already indicated, this support bar 53 may be attached to the front or rear frame part 4,5 (as shown) or may be an integral part of the front or rear frame part 4,5 (not shown).

FIG. 14B is showing a detent bolt positioned below the replaceable tabletop element and being configured to be movable with respect to the replaceable tabletop element and in direction of the bolt axis. In particular, it is shown that a front detent bolt 10 (it also may be a rear detent bolt 11) is positioned below the replaceable tabletop element 3. The detent bolt 10 has a bolt axis 26 that extends parallel to a tabletop axis 27 of the tabletop element 3. The detent bolt 10,11 is configured for horizontal insertion into a slit 55 of a detent rail or detent element 6,6',7,7' at one or both of the front and rear frame parts 4,5. Such a detent element 6,6',7,7' may be attached to the front or rear frame part 4,5 (as shown) or may be an integral part of the front or rear frame part 4,5 (not shown). Preferably, such a detent bolt 10,11 is configured to be movable with respect to the replaceable tabletop element 3 and in direction of the bolt axis 26 (see double arrow) and in an oblong hole 15'. It is further preferred that such a detent bolt 10,11 is configured for horizontal insertion into a slit 55 of a detent rail or detent element 6,6',7,7' at one or both of the front and rear frame parts 4,5. In consequence, such a detent bolt 10,11 is also configured as a fixing mechanism 20 that fixes the tabletop element 3 against horizontal or vertical movements.

Indicated in the top view of FIG. 14A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown).

The third and fourth additional embodiments of detent bolts 10,11 and fixing mechanisms 20 allow vertically inserting the detent bolts 10,11 in the holes 52 of the support bars 53. Also fixing the tabletop elements 3 in this insert position is provided by the fixing mechanisms 20 disclosed in FIG. 14. In consequence, horizontal movement of the tabletop elements 3 is not necessary and practically the entire area between the front and rear frame parts 4,5 may be covered by the tabletop elements 3. Thus, only a small gap may be left between the front and rear frame parts 4,5 and the tabletop elements 3.

FIG. 15A-15B shows vertical section and top views of fifth and sixth additional embodiments of detent bolts and fixing mechanisms.

FIG. 15A is showing a detent bolt that is rotatably attached to the tabletop element and comprising a key element configured for insertion into an oblong hole. In particular, it is shown that a front detent bolt 10 (it may be as well a rear detent bolt 11) has a bolt axis 26 that extends perpendicular to the replaceable tabletop element 3. The front or rear detent bolt 10,11 is rotatably attached to the tabletop element 3 and comprises a key element 54 with a groove 14. The key element 54 is configured for insertion into an oblong hole 15' (see top view) in a holding web 13 of a support bar 53 and for being turned about the bolt axis 26 in a way that the holding web 13 engages with the groove 14.

In consequence, such a rotatably attached detent bolt 10,11 with a key element 54 and a groove 14 in a combination with oblong hole 15' in a holding web 13 of a support bar 53 is also configured as a fixing mechanism 20 that fixes the tabletop element 3 against horizontal or vertical movements.

Preferably, the replaceable tabletop element 3 comprises, on a front or rear side 66,67 and distant to the detent bolt 10,11 that is rotatably attached to the tabletop element 3, at least one rear or front detent bolt 11,10 that is:
(i) implemented as nose extension 61 of the tabletop element 3 (see FIGS. 16A-19B), or
(ii) positioned below the tabletop element 3 and having a bolt axis 26 that extends parallel to a tabletop axis 27 of the tabletop element 3 (see FIG. 15B).

FIG. 15B is showing a detent bolt that is immovably positioned below the replaceable tabletop element and configured for horizontal insertion into a slit. In particular, it is shown that the detent bolt 10 has a bolt axis 26 that extends parallel to a tabletop axis 27 of the tabletop element 3. The detent bolt 10,11 is configured for horizontal insertion into a slit 55 of a detent rail or detent element 6,6',7,7' at one or both of the front and rear frame parts 4,5. Such a detent element 6,6',7,7' may be attached to the front or rear frame part 4,5 (as shown) or may be an integral part of the front or rear frame part 4,5 (not shown). Preferably, such a detent bolt 10,11 is configured to be movable together with the replaceable tabletop element 3 and in direction of the bolt axis 26 (see double arrow). It is further preferred that such a detent bolt 10,11 is configured for horizontal insertion into a slit 55 of a detent rail or detent element 6,6',7,7' at one or both of the front and rear frame parts 4,5.

In consequence, a combination of such a detent bolt 10,11 with a slit in a detent rail or detent element 6,6',7,7' attached to a front or rear frame part 4,5 or with a slit in a front or rear frame part 4,5 is also configured as a fixing mechanism 20 that fixes the tabletop element 3 against horizontal or vertical movements.

The fifth additional embodiment with rotatably attached detent bolts 10,11 and fixing mechanisms 20 allow vertically inserting the detent bolts 10,11 in the oblong holes 15' of the support bars 53. Also fixing the tabletop elements 3 in this insert position is provided by the fixing mechanisms 20 disclosed in FIG. 15A. In consequence, horizontal movement of the tabletop elements 3 is not necessary and practically the entire area between the front and rear frame parts 4,5 may be covered by the tabletop elements 3. Thus, only a small gap may be left between the front and rear frame parts 4,5 and the tabletop elements 3.

The combination of the fifth and sixth additional embodiment however, makes it necessary to first insert the detent bolts 10,11 configured for horizontal insertion into a slit 55 of a detent rail or detent element 6,6',7,7' at one or both of the front and rear frame parts 4,5. This results in horizontal movements of the tabletop elements 3 (see double arrow and on-sided bold arrow). Subsequently, the rotatably attached detent bolts 10,11 and fixing mechanisms 20 are vertically inserted into the oblong holes 15' and than preferably turned by 90° around the detent bolt axis 26. Because of this, not the entire area between the front and rear frame parts 4,5 may be covered by the tabletop elements 3 and a broader gap may be left between the front or rear frame parts 4,5 and the tabletop elements 3.

In consequence, such rotatably attached detent bolts 10,11 and detent bolts 10,11 configured for horizontal insertion a combination of with a slit in a detent rail or detent element 6,6',7,7' attached to a front or rear frame part 4,5 or with a slit in a front or rear frame part 4,5 is also configured as a fixing mechanism 20 that fixes the tabletop element 3 against horizontal or vertical movements.

Indicated in the top view of FIG. 15A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown). FIG. 16A-16B shows vertical section and top views of seventh and eighth additional embodiments of detent bolts and fixing mechanisms.

FIG. 16A is showing a detent bolt 10 immovably extending perpendicular to the replaceable tabletop element 3 and comprising a key element 54 configured for insertion into an oblong hole 15'. In particular, it is shown that a front detent bolt 10 (it could also be a rear detent bolt 11) has a bolt axis 26 that extends perpendicular to a tabletop axis 27 of the replaceable tabletop element 3. The front or rear detent bolt 10,11 is immovably attached to the tabletop element 3 and comprises a key element 54 with a groove 14. The key element 54 is configured for insertion into an oblong hole 15' in a holding web 13 of a support bar 53 (see top view) and for being moved together with the tabletop element 3 in direction of the tabletop axis 27 of the tabletop element 3 in a way that the holding web 13 engages with the groove 14.

In consequence, such an attached detent bolt 10,11 with a key element 54 and a groove 14 in a combination with oblong hole 15' in a holding web 13 of a support bar 53 is also configured as a fixing mechanism 20 that fixes the tabletop element 3 against horizontal or vertical movements.

FIG. 16B is showing a detent bolt implemented as nose extension of the tabletop element and a fixing mechanism configured as an eccentric lock element. In particular, it is shown that the replaceable tabletop element 3 further comprises a fixing mechanism 20 configured as an eccentric lock element 56. This eccentric lock element 56 is configured for rotation about an axis 63 and for acting on a rear surface 62 of one of the support bars 53, the front frame part 4, or rear frame part 5. As a reaction of turning the eccentric lock element 56 into the locking position, the tabletop element 3 and the key element 54 of the front detent bolt 10 (or rear detent bolt 11, as the case may be) in direction of the tabletop axis 27 (see bold arrow).

Preferably, at least some of the detent bolts 10,11 (here detent bolt 11) are implemented as nose extensions 61 of the replaceable tabletop element 3. It is further preferred that the front or rear detent bolt 10,11 is configured for horizontal insertion into a slit 55 of a detent rail or detent element 6,6',7,7' at one or both of the front and rear frame parts 4,5 (here at the rear frame part 7).

In consequence, such immovably attached detent bolts 10,11 and detent bolts 10,11 configured for horizontal insertion in combination of with a slit in a detent rail or detent element 6,6',7,7' attached to a front or rear frame part 4,5 (or with a slit in a front or rear frame part 4,5, as the case may be) is also configured as a fixing mechanism 20 that fixes the tabletop element 3 against horizontal or vertical movements.

Indicated in the top view of FIG. 16A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown).

FIG. 17A-17B shows vertical section and top views of ninth and tenth additional embodiments of detent bolts and fixing mechanisms.

FIG. 17A is showing a fixing mechanism configured as a lock profile for displacing all present replaceable tabletop elements in direction of the tabletop axis. In particular, it is shown that the laboratory table 1 comprises a fixing mechanism 20 configured as a lock profile 57 for attachment to a front frame part 4 or to a rear frame part 5. Such attachment preferably is carried out by means of a box lock arrangement 64. Such box locks 64 are known per se and may be opened and closed manually. Such attachment of a lock profile 57 is carried out in a way to one of the front or rear frame parts 4,5 that results in displacing all present replaceable tabletop elements 3 and their key elements 54 of the front or rear detent bolts 10,11 in direction of the tabletop axis 27 (see bold arrow).

Preferably, the lock profile 57 comprises an extension 61' that reaches over the front or rear side of the replaceable tabletop element 3 in order to prohibit vertical movements of the replaceable tabletop element 3 that is placed on the front and rear frame parts 4,5.

In consequence, such a fixing mechanism 20 configured as a lock profile 57 may be attached to a front frame part 4 and/or to a rear frame part 5 in a way that the lock profile 57 in a lock position fixes all present replaceable tabletop elements 3 and prevents these tabletop elements 3 from horizontal and/or vertical movements.

FIG. 17B is showing a detent bolt 11 implemented as nose extension 61 of a replaceable tabletop element 3 and configured for horizontal insertion into a slit 55 or oblong hole 15' in one of the front or rear frame parts 4,5 (here in the rear frame part 5). In particular, it is shown that the replaceable tabletop element 3 is moved in direction of the table top axis 27 until the nose extension 61 enters the slit 55 or oblong hole 15' in one of the front or rear frame parts 4,5.

In consequence, such immovably attached detent bolts 10,11 and detent bolts 10,11 configured as nose extensions 61 of the table top elements 3 for horizontal insertion a combination of with a slit 55 in a detent rail or detent element 6,6',7,7' attached to a front or rear frame part 4,5 (or with a slit 55 in a front or rear frame part 4,5, as the case may be) is also configured as a fixing mechanism 20 that fixes the tabletop element 3 against horizontal or vertical movements.

Indicated in the top view of FIG. 17A by the number 62 is the rear surface of the front frame part 4. This front frame part 4 is carrying the front side 66 of the tabletop element 3.

Generally, utilizing a combination of nose extensions 61 of the table top elements 3 and corresponding slits 55 or oblong holes 15' in one of the front or rear frame parts 4,5 (in each case at a regular distance 12) defines the same modular grid as earlier described by the combination and arrangement of detent openings 8,8',9,9' and detent bolts 10,11 arranged at the same regular distance.

FIG. 18A-18B shows vertical section and top views of eleventh and twelfth additional embodiments of detent bolts and fixing mechanisms.

FIG. 18A is showing a detent bolt 10 immovably extending perpendicular to the replaceable tabletop element 3 and comprising a key element 54 configured for insertion into an oblong hole 15'. In particular, it is shown that a front detent bolt 10 (it could also be a rear detent bolt 11) has a bolt axis 26 that extends perpendicular to a tabletop axis 27 of the replaceable tabletop element 3. The front or rear detent bolt 10,11 is immovably attached to the tabletop element 3 and comprises a key element 54 with a groove 14. The key element 54 is configured for insertion into an oblong hole 15' in a holding web 13 of a support bar 53 (see top view) and for being moved together with the tabletop element 3 in direction of the tabletop axis 27 of the tabletop element 3 in a way that the holding web 13 engages with the groove 14.

In consequence, such an attached detent bolt 10,11 with a key element 54 and a groove 14 in a combination with oblong hole 15' in a holding web 13 of a support bar 53 is also configured as a fixing mechanism 20 that fixes the tabletop element 3 against horizontal or vertical movements.

FIG. 18B is showing a fixing mechanism configured as a lock slide which in a locking position abuts a detent bolt and thus blocks the replaceable tabletop element in direction of the tabletop axis. In particular, it is shown that the laboratory table 1 further comprises a fixing mechanism 20 configured as a lock slide 58 situated slidable at a detent rail or detent element 6,6',7,7'. Moving the tabletop element 3 in direction of the table top axis 27 (see bold arrow in the top view) and sliding of the lock slide 58 horizontally in a direction perpendicular to the tabletop axis 27 and into a locking position results in abutting a rear detent bolt 11 or front detent bolt 10. Thus blocking the replaceable tabletop element 3 and the key element 54 of the front detent bolt 10 or rear detent bolt 11 in direction of the tabletop axis 27 occurs.

Preferably, at least some of the detent bolts 10,11 (here rear detent bolt 11) are implemented as nose extensions 61 of the replaceable tabletop element 3. It is further preferred that the front or rear detent bolt 10,11 is configured for horizontal insertion into a slit 55 of a detent rail or detent element 6,6',7,7' at one or both of the front and rear frame parts 4,5 (here at the rear detent rail 7).

Indicated in the top view of FIG. 18A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown).

In consequence, such immovably attached detent bolts 10,11 and detent bolts 10,11 configured as nose extensions 61 of the table top elements 3 for horizontal insertion in combination with a slit 55 in a detent rail or detent element 6,6',7,7' attached to a front or rear frame part 4,5 (or with a slit 55 in a front or rear frame part 4,5, as the case may be) is also configured as a fixing mechanism 20 that fixes the tabletop element 3 against horizontal or vertical movements.

FIG. 19A-19B shows vertical section and top views of thirteenth and fourteenth additional embodiments of detent bolts and fixing mechanisms.

FIG. 19A is showing a detent bolt immovably extending perpendicular to the replaceable tabletop element and comprising a key element configured for insertion into an oblong hole. In particular, it is shown that a front detent bolt 10 (it could also be a rear detent bolt 11) has a bolt axis 26 that extends perpendicular to a tabletop axis 27 of the replaceable tabletop element 3. The front or rear detent bolt 10,11 is immovably attached to the tabletop element 3 and comprises a key element 54 with a groove 14. The key element 54 is configured for insertion into an oblong hole 15' in a holding web 13 of a support bar 53 (see top view) and for being moved together with the tabletop element 3 in direction of the tabletop axis 27 of the tabletop element 3 in a way that the holding web 13 engages with the groove 14.

In consequence, such an attached detent bolt 10,11 with a key element 54 and a groove 14 in a combination with oblong hole 15' in a holding web 13 of a support bar 53 is also configured as a fixing mechanism 20 that fixes the tabletop element 3 against horizontal or vertical movements.

FIG. 19B is showing a detent opening configured as cut-out part which is implemented for receiving a nose extension of a replaceable tabletop element. In particular, it is shown that at least some of the detent openings 8,8',9,9' that are arranged at the front or rear frame part 4,5 are configured as cut-out parts 49 which are implemented for receiving a nose extension 61 of a replaceable tabletop element 3.

The cut-out parts 49 have a cut-out part axis 50 that extends parallel to a tabletop axis 27 of the replaceable tabletop element 3.

For positioning a tabletop element 3 on the laboratory table 1, the front detent bolts 10 preferably are inserted into the oblong holes 15' of the support bar 53 and then the tabletop element 3 is moved in direction of the tabletop axis 27 until the nose extensions 61 of the replaceable tabletop element 3 come to lay in the cut-out parts 49. In this position, the tabletop element 3 is fixed in all horizontal directions. It is further preferred that a lock slide 58 is movable over the cut-out parts 49 and the nose extension 61 of a replaceable tabletop element 3 that is positioned on the front and rear frame parts 4,5. Moving the tabletop element 3 in direction of the table top axis 27 (see bold arrow in the top view) and sliding of the lock slide 58 horizontally into a direction parallel to the tabletop axis 27 and into a locking position results in fixing the tabletop element 3 also in vertical direction.

Indicated in the top view of FIG. 19A by the number 62 is the rear surface of the support bar 53. This support bar 53 is carrying the front side 66 of the tabletop element 3. This support bar 53 may be attached to the front or rear frame part 4,5 (as shown) or may be an integral part of the front or rear frame part 4,5 (not shown).

In consequence, such immovably attached detent bolts 10,11 and detent bolts 10,11 configured as nose extensions 61 of the table top elements 3 for horizontal insertion in combination with a cut-out part 49 in a detent rail or detent element 6,6',7,7' attached to a front or rear frame part 4,5 (or with a cut-out part 49 in a front or rear frame part 4,5, as the case may be) is also configured as a fixing mechanism 20 that fixes the tabletop element 3 against horizontal or vertical movements.

FIG. 20A-20B shows vertical section and top views of fifteenth and sixteenth additional embodiments of detent bolts and fixing mechanisms.

FIG. 20A is showing a detent bolt implemented as a screw captive (but of course rotatable) incorporated to the replaceable tabletop element. In particular, it is shown that the font detent bolt 10 is implemented as screw 68 that is captive incorporated to the replaceable tabletop element 3. Preferably in order to achieve a flat tabletop surface and to ease cleaning of the tabletop surface, the screw head may be covered by a plastic cover 65. The screw 68 could be turned into the front or rear frame part 4,5 and could also be provided separately with the replaceable tabletop elements 3.

The mating screw threads in the front and/or rear part frames 4,5 that are accommodating the screws 68 are regarded as a synonym to the already mentioned detent openings 8,8',9,9'. Thus, utilizing a combination of screws 68 for fixing the table top elements 3 and corresponding mating screw threads in the front and/or rear frame parts 4,5 (in each case at a regular distance 12) defines the same modular grid as earlier described by the combination and arrangement of detent openings 8,8',9,9' and detent bolts 10,11 arranged at the same regular distance.

Indicated in the top view of FIG. 20A by the number 62 is the rear surface of the front frame part 4. This front frame part 4 is carrying the front side 66 of the tabletop element 3.

In consequence, a combination of such screws 68 with mating screw threads in the front and/or rear part frames 4,5 is also configured as a fixing mechanism 20 that fixes the tabletop element 3 against horizontal or vertical movements.

FIG. 20B is showing a detent bolt implemented as a pin captive attached to the replaceable tabletop element. In particular, it is shown that at least some of the detent bolts 10,11 are implemented as pins 70 that are captive incorporated to the replaceable tabletop elements 3.

The mating holes or shells in the front and/or rear part frames 4,5 that are accommodating the pins 70 are regarded as a synonym to the already mentioned detent openings 8,8',9,9'. Thus, utilizing a combination of pins 70 for fixing the table top elements 3 and corresponding mating screw threads in the front and/or rear frame parts 4,5 (in each case at a regular distance 12) defines the same modular grid as earlier described by the combination and arrangement of detent openings 8,8',9,9' and detent bolts 10,11 arranged at the same regular distance.

The tabletop elements 3 preferably are made of stainless steel and are of considerable weight. If however the weight of a tabletop element 3 with e.g. a thickness of 0.4 to 0.8 cm is not sufficient for keeping the tabletop element 3 in place against lifting forces (as applied e.g. by a robot attached to or working with the laboratory table), the thickness of the tabletop element 3 may be increased as required for reaching a particular weight. Tabletop elements 3 with very small size preferably have increased weight, if they are only equipped with pins 70.

Indicated in the top view of FIG. 20B by the number 62 is the rear surface of the rear frame part 5. The rear frame part 5 is carrying the rear side 67 of the tabletop element 3.

In consequence, a combination of such pins 70 (potentially attached to tabletop elements 3 with increased weight) with mating holes or shells in the front and/or rear part frames 4,5 is also configured as a fixing mechanism 20 that fixes the tabletop element 3 against horizontal or vertical movements.

The mating holes or shells in the front and/or rear part frames 4,5 that are accommodating the pins 70 are regarded as a synonym to the already mentioned detent openings 8,8',9,9'. Thus, utilizing a combination of pins 70 for fixing the table top elements 3 and corresponding mating holes or shells in the front and/or rear frame parts 4,5 (in each case at a regular distance 12) defines the same modular grid as earlier described by the combination and arrangement of detent openings 8,8',9,9' and detent bolts 10,11 arranged at the same regular distance.

FIG. 21A-21B shows vertical section and top views of seventeenth and eighteenth additional embodiments of detent bolts and fixing mechanisms. In particular, it is shown a laboratory table 1 comprising a front frame part 4 and a rear frame part 5 opposite thereto. This laboratory table 1 further comprises replaceable tabletop elements 3 positionable on these front and rear frame parts 4,5. Each tabletop element 3 of the laboratory table 1 comprises at least one detent opening 8,8',9,9' on a front side 66 and/or on a rear side 67 of the tabletop element 3, each of these detent openings 8,8',9,9' being implemented and arranged for insertion of a detent bolt 10,11. The front frame part 4 and/or the rear frame part 5 of the laboratory table 1 comprise a number of detent bolts 10,11 that are arranged at a regular distance 12 defining a modular grid, each one of the detent bolts 10,11 being implemented and arranged for insertion into one of the detent openings 8,8',9,9' of the tabletop elements 3 positioned on these front and rear frame parts 4,5.

Though not imperative, it is particularly preferred that each one of these detent openings 8,8',9,9' is also implemented and arranged for sliding guiding of a detent bolt 10,11 of the front frame part 4 and/or the rear frame part 5 of the laboratory table 1. This preference applies to all sorts of detent bolts 10,11 whether they are implemented as e.g. pins, screws, noses, projections, or slides and whether they are orientated vertically or horizontally or slightly deviating from horizontal or vertical orientation.

It may be preferred that the laboratory table 1 comprises fixing mechanisms 20 that are configured for fixing the replaceable tabletop elements 3 positioned on these front and rear frame parts 4,5 in a locking position, said fixing mechanisms 20 being:
  attached to or integrated in a replaceable tabletop element 3, or
  attached to or integrated in a detent bolt 10,11, or
  attached to or integrated in a detent rail or detent element 6,6',7,7', or
  attached to or integrated in a front frame part 4 or rear frame part 5.

It is shown in the FIG. 20A-20B that the detent openings 8,8',9,9' of the tabletop element 3 preferably are configured as slits 55 or oblong holes 15' that extend from a front side 66 or a rear side 67 of the tabletop element 3 and parallel to a tabletop axis 27 of the tabletop element 3.

It is further shown in the FIG. 20A-20B that the front or rear frame part 4,5 of the laboratory table 1 comprises a fixing mechanism 20 preferably configured as a lock profile 57 that is tiltable against a force of a spring 59 and about an axis 63 which preferably is fixed to the front or rear frame part 4,5.

FIG. 21A is showing a detent opening of a tabletop element configured as oblong hole that extends at a side of the tabletop element, a detent bolt is arranged on a frame part, and a fixing mechanism is configured as a tiltable lock profile. In particular, it is shown that the detent bolts 10,11 of the laboratory table 1 are arranged at a regular distance 12 on the front frame part 4 and/or on the rear frame part 5, the regular distance 12 defining a modular grid, each of these detent bolts 10,11 being implemented and arranged for insertion into a detent opening 8,8',9,9' of a tabletop element 3.

Preferably, the detent bolts 10,11 of the laboratory table 1 are arranged at a regular distance 12 on the front and/or rear frame part 4,5.

Indicated in the top view of FIG. 21A by the number 62 is the rear surface of the front frame part 4. This front frame part 4 is carrying the front side 66 of the tabletop element 3.

Preferably, the lock profile 57 is configured and arranged to cover the detent openings 8,8',9,9' of the replaceable tabletop element 3 positioned on these front and rear frame parts 4,5 and to prevent the tabletop element 3 from vertical movements when the lock profile 57 is in a locking position.

In consequence, a combination of such detent bolts 10,11 at the front and/or rear part frames 4,5 and detent openings 8,8',9,9' of the replaceable tabletop elements 3 with the provision of a lock profile 57 is also configured as a fixing mechanism 20 that fixes the tabletop element 3 against horizontal or vertical movements.

FIG. 21B is showing a detent opening of a tabletop element configured as slit that extends from a side of the tabletop element, a detent bolt is arranged on a fixing mechanism is configured as a tiltable lock profile. In particular, it is shown that the detent bolts 10,11 of the laboratory table 1 are arranged at a regular distance 12 on a fixing mechanism 20 configured as a lock profile 57 that is tiltable against a force of a spring 59 and about an axis 63 which is fixed to the front or rear frame part 4,5.

Indicated in the top view of FIG. 21B by the number 62 is the rear surface of the rear frame part 5. The rear frame part 5 is carrying the rear side 67 of the tabletop element 3.

In the locking position of the fixing mechanisms 20, the detent bolts 10,11 are configured and arranged to extend within the detent openings 8,8',9,9' of a replaceable tabletop element 3 positioned on these front and rear frame parts 4,5 and perpendicular to the tabletop element 3.

In consequence, a combination of such detent bolts 10,11 attached to a lock profile 57 and detent openings 8,8',9,9' of the replaceable tabletop elements 3 is also configured as a fixing mechanism 20 that fixes the tabletop element 3 against horizontal or vertical movements.

Generally, utilizing a combination of detent bolts 10,11 of the table top elements 3 or of the lock profiles 57 and corresponding slits 55 or oblong holes 15' in the replaceable tabletop elements 3 defines the same modular grid as earlier described by the combination and arrangement of detent openings 8,8',9,9' and detent bolts 10,11 arranged at the same regular distance.

It is particularly noted that each table top element 3 may comprise oblong holes 15' that extend at its front side 66 and at its rear side 67. It may be also preferred that each table top element 3 comprises slits 55 that extend from its front side 66 and from its rear side 67. Also any arbitrary mix of oblong holes 15' and slits 55 for one single table top element 3 is possible, e.g. providing oblong holes 15' at its front side 66 and slits 55 at its rear side 67 or vice versa. Also alternating oblong holes 15' and slits 55 at the front side 66 and/or at the rear side 67 of a table top element 3 is feasible. A combination of oblong holes 15' or slits 55 on one side of the table top element 3 and a circular hole on its other side (not shown) may also be preferred.

Above all, it is important that the detent openings 8,8',9,9' and detent bolts 10,11 are arranged at a regular distance 12, thus defining a modular grid.

Identical reference signs relate to corresponding features, even if they are not described in detail in each case. Arbitrary combinations of the embodiments and variants which are described and/or shown are within the scope of the present invention.

| List of reference numerals | |
|---|---|
| 1 | laboratory table |
| 2 | frame |
| 3 | tabletop element |
| 4 | front frame part |
| 5 | rear frame part |
| 6 | upper front detent rail |
| 6' | lower front detent rail |
| 7 | upper rear detent rail |
| 7' | lower rear detent rail |
| 8 | upper front detent opening |
| 8' | lower front detent opening |
| 9 | upper rear detent opening |
| 9' | lower rear detent opening |
| 10 | front detent bolt |
| 11 | rear detent bolt |
| 12 | regular distance |
| 13 | first holding web |
| 13' | second holding web |
| 14 | groove |
| 15 | recess |
| 15' | oblong hole |
| 16 | largest cross section of 10, 11 |
| 17 | reduced cross section of 10, 11 |
| 18 | constriction |
| 19 | stop surface |
| 20 | fixing mechanism |
| 20' | clamping lever |
| 21 | lower side of 3 |
| 22 | table inner side |
| 23 | table outer side |
| 24 | further frame part25 further frame part |
| 26 | bolt axis |
| 27 | tabletop axis |
| 28 | infeed chamfer |
| 29 | upper tabletop level |
| 30 | lower tabletop level |
| 31 | holding rail |
| 32 | detent cam |
| 33 | reinforcement bracket |
| 34 | clamping bow |
| 35 | fixing block |
| 36 | handle |
| 37 | axis |
| 38 | rear wall |
| 39 | recess axis |
| 40 | cutout |
| 41 | over-twisting guard |
| 42 | holding portion |
| 43 | width of 3 |
| 44 | joint |
| 45 | flip part of 10, 11 |
| 46 | axis, eccentric axis of 45 |
| 47 | guide |
| 48 | magnet (electric, switchable permanent, or permanent) |
| 49 | cut-out part |
| 50 | cut-out part axis |
| 51 | magnetizable material |
| 52 | hole |
| 53 | support bar |
| 54 | key element |
| 55 | slit |
| 56 | eccentric lock element |
| 57 | lock profile |
| 58 | lock slide |
| 59 | spring |
| 60 | ring, grip, handle |
| 61 | nose extension of 3 |
| 61' | extension |
| 62 | rear surface of 4, 5, or 53 |
| 63 | axis of 56 or 57 |
| 64 | box lock |
| 65 | plastic cover |
| 66 | front side of 3 |
| 67 | rear side of 3 |
| 68 | screw |
| 69 | turned down portion |
| 70 | pin |

The invention claimed is:

1. A laboratory table (1) comprising:
   (a) a front frame part (4) and a rear frame part (5) opposite thereto, said front and rear frame parts (4,5) being arranged parallel to one another and aligned essentially horizontally;
   (b) replaceable tabletop elements (3) positionable on said front and rear frame parts (4,5), each replaceable tabletop element (3) being smaller in at least one horizontal dimension than said front and rear frame parts (4,5);
   (c) a number of detent openings (8,8',9,9') arranged at a regular distance (12) on the front frame part (4) and/or on the rear frame part (5), said regular distance (12) defining a modular grid, each of these detent openings (8,8',9,9') being implemented and arranged for insertion of a detent bolt (10,11) of a replaceable tabletop element (3) positioned on said front and rear frame parts (4,5); and
   (d) fixing mechanisms (20) that are configured for fixing said replaceable tabletop elements (3) positioned on said front and rear frame parts (4,5) in a locking position,
   wherein each replaceable tabletop element (3) has a width (43) that at least approximately corresponds to a multiple of said regular distance (12) and that is configured as a modular tabletop element (3), which comprises at least four detent bolts (10,11);
   wherein said at least four detent bolts (10,11) are arranged in groups, each group of detent bolts (10,11) being linearly arranged, and implemented for insertion into respective detent openings (8,8',9,9') that are linearly arranged on said front and/or rear frame parts (4,5) of the laboratory table (1); and
   wherein said at least four detent bolts (10,11) are arranged at said regular distance (12) or in a multiple of said regular distance (12).

2. The laboratory table (1) according to claim 1, wherein the at least four detent bolts (10,11) are implemented as captive and are immovably connected fixed in place to the respective tabletop element (3).

3. The laboratory table (1) according to claim 1, wherein the at least four detent bolts (10,11) are implemented as rotatable around a bolt axis (26) and are connected fixed in place to the replaceable tabletop element (3).

4. The laboratory table (1) according to claim 1, wherein the at least four detent bolts (10,11) have a cylindrical shape having continuously identical cross section.

5. The laboratory table (1) according to claim 1, wherein the laboratory table (1) comprises replaceable tabletop elements (3) in an upper tabletop level (29) and/or in a lower tabletop level (30), all replaceable tabletop elements (3) being aligned essentially horizontally in the installed state.

6. The laboratory table (1) according to claim 1, wherein the frame parts (4,5) arranged opposite to one another are arranged parallel to one another, and wherein a frame (2) comprises said front and rear frame parts (4,5) and two further frame parts (24,25) and is implemented as a rectangular frame (2).

7. The laboratory table (1) according to claim 1, wherein at least two of said at least four detent bolts (10,11) are implemented as nose extensions (61) of the replaceable tabletop elements (3), and wherein at least two of the detent openings (8,8',9,9') that are arranged at the front or rear frame part (4,5) are configured as cut-out parts (49) which are implemented for receiving said at least two nose extensions (61) of a replaceable tabletop element (3).

8. The laboratory table (1) according to claim 7, wherein said at least two detent openings (8,8',9,9') have a cut-out part axis (50) that extends parallel to a tabletop axis (27) of the replaceable tabletop element (3).

9. The laboratory table (1) according to claim 1, wherein at least some of the detent bolts (10,11) are implemented as screws (68) that are captive incorporated to the replaceable tabletop elements (3) or that are separately provided with the replaceable tabletop elements (3).

10. The laboratory table (1) according to claim 1, wherein a front detent bolt (10) or rear detent bolt (11) has a bolt axis (26) extending perpendicular to the replaceable tabletop element (3), the front detent bolt (10) or rear detent bolt (11) comprising a fixing mechanism (20) configured as a flip part (45) that is tiltably mounted to a detent bolt (10,11) by an axis (46), the front detent bolt (10) or rear detent bolt (11) all over having a substantially continuous cross section when the flip part (45) is being hold in an insert position for positioning, by a penetrated hole (52), on or removing, manually or by a guide (47) or by a magnet (48), a tabletop element (3) from said front and rear frame parts (4,5).

11. The laboratory table (1) according to claim 10, wherein in the insert position, the flip part (45) is biased with respect to the front or rear detent bolt (10,11) by a spring (59), biasing causing the flip part (45) to flip about its axis (46) into a locking position in which the flip part (45) protrudes beyond the substantially continuous cross section of the front detent bolt (10) or rear detent bolt (11).

12. The laboratory table (1) according to claim 11, wherein the flip part (45) is configured to be hold in the insert position manually or by a guide (47) positioned below the replaceable tabletop element (3).

13. The laboratory table (1) according to claim 10, wherein the flip part (45) is mounted tiltable about an eccentric axis (46) and comprises magnetizable material, gravity of the flip part (45) causing the flip part (45) to flip about its eccentric axis (46) into a locking position, in which the flip part (45) protrudes beyond the substantially continuous cross section of the front or rear detent bolt (10,11).

14. The laboratory table (1) according to claim 13, wherein the flip part (45) is configured to be hold in the insert position manually, by a guide (47), or by a magnet (48) positioned on the replaceable tabletop element (3).

15. The laboratory table (1) according to claim 1, wherein a front detent bolt (10) or rear detent bolt (11) has a bolt axis (26) extending perpendicular to the replaceable tabletop element (3) and is implemented for insertion into a hole (52) of a support bar (53) or of the front or rear frame parts (4,5) of the laboratory table (1), the front or rear detent bolt (10,11) comprising a turned down portion (69) that is implemented to be acted on by at least one spring (59) attached to said support bar (53) or said front or rear frame parts (4,5) of the laboratory table (1).

16. The laboratory table (1) according to claim 15, wherein the front or rear detent bolt (10,11) has a cylindrical shape comprising the turned down portion (69).

17. The laboratory table (1) according to claim 1, wherein a front detent bolt (10) or rear detent bolt (11) is positioned below the replaceable tabletop element (3) and has a bolt axis (26) that extends parallel to a tabletop axis (27) of the tabletop element (3), the front or rear detent bolt (10,11) being configured for horizontal insertion into a slit (55) of a detent rail or detent element (6,6',7,7') at one or both of the front and rear frame parts (4,5) of the laboratory table (1).

18. The laboratory table (1) according to claim 17, wherein the front detent bolt (10) or rear detent bolt (11) is configured to be movable with respect to the replaceable tabletop element (3) and in direction of the bolt axis (26).

19. The laboratory table (1) according to claim 1, wherein a front detent bolt (10) or rear detent bolt (11) is positioned below the replaceable tabletop element (3) and has a bolt axis (26) that extends perpendicular to the tabletop element (3), the front or rear detent bolt (10,11) comprising magnetizable material (51) or a magnet (48) and being configured to be positioned in a hole (52) of a support bar (53) of the laboratory table (1) that comprises magnetizable material (51) or a magnet (48).

20. The laboratory table (1) according to claim 19, wherein the magnet (48) comprised by the support bar (53) of the laboratory table (1) is selected from a group comprising permanent magnets, electromagnets, and switchable permanent magnets.

21. The laboratory table (1) according to claim 1, wherein a front detent bolt (10) or rear detent bolt (11) has a bolt axis (26) that extends perpendicular to the replaceable tabletop element (3), the front or rear detent bolt (10,11) being rotatably attached to the tabletop element (3) and comprising an oblong key element (54) with a groove (14), the oblong key element (54) being configured for insertion into an oblong hole (15') in a holding web (13) of a support bar (53) of the laboratory table (1) and for being turned about the bolt axis (26) in a way that the holding web (13) engages with the groove (14).

22. The laboratory table (1) according to claim 21, wherein the replaceable tabletop element (3) comprises, on a front or rear side (66,67) and distant to said detent bolt (10,11) that is rotatably attached to the tabletop element (3), at least one rear or front detent bolt (11,10) that is:
(i) implemented as nose extension (61) of the tabletop element (3), or
(ii) positioned below the tabletop element (3) and having a bolt axis (26) that extends parallel to a tabletop axis (27) of the tabletop element (3).

23. The laboratory table (1) according to claim 1, wherein the front or rear detent bolt (10,11) is configured for horizontal insertion into a slit (55) of a detent rail or detent element (6,6',7,7') at one or both of the front and rear frame parts (4,5) of the laboratory table (1).

24. The laboratory table (1) according to claim 1, wherein a front detent bolt (10) or rear detent bolt (11) has a bolt axis (26) that extends perpendicular to the replaceable tabletop element (3), the front or rear detent bolt (10,11) being immovably attached to the tabletop element (3) and comprising an oblong key element (54) with a groove (14), the oblong key element (54) being configured for insertion into an oblong hole (15') in a holding web (13) of a support bar (53) of the laboratory table (1) and for being moved together with the tabletop element (3) in direction of a tabletop axis (27) of the tabletop element (3) in a way that the holding web (13) engages with the groove (14).

25. The laboratory table (1) according to claim 24, wherein the replaceable tabletop element (3) further comprises a fixing mechanism (20) configured as an eccentric lock element (56) that is configured for rotation about an axis (63) and for acting on a rear surface (62) of one of the support bar (53), the front frame part (4), or rear frame part (5) and thus for moving the tabletop element (3) and the oblong key element (54) of the front detent bolt (10) or rear detent bolt (11) in direction of the tabletop axis (27).

26. The laboratory table (1) according to claim 24, wherein the laboratory table (1) further comprises a fixing mechanism (20) configured as a lock profile (57) for attachment to a front frame part (4) or to a rear frame part (5) in a way that attachment of the lock profile (57) to one of the front or rear frame parts (4,5) results in displacing all present replaceable tabletop elements (3) and their oblong key elements (54) of the front or rear detent bolts (10,11) in direction of the tabletop axis (27).

27. The laboratory table (1) according to claim 24, wherein the laboratory table (1) further comprises a fixing mechanism (20) configured as a lock slide (58) situated slidable at a detent rail or detent element (6,6',7,7') in a way that sliding of the lock slide (58) in a direction perpendicular to the tabletop axis (27) and into a locking position results in abutting a rear detent bolt (11) or front detent bolt (10) thus blocking the replaceable tabletop element (3) and the oblong key element (54) of the front detent bolt (10) or rear detent bolt (11) in direction of the tabletop axis (27).

28. The laboratory table (1) according to claim 1, wherein a front detent bolt (10) or rear detent bolt (11) has a bolt axis (26) that extends perpendicular to the replaceable tabletop element (3), the front or rear detent bolt (10,11) being immovably attached to the tabletop element (3).

29. A laboratory table (1) comprising:
(a) a front frame part (4) and a rear frame part (5) opposite thereto, said front and rear frame parts (4,5) being arranged parallel to one another, being aligned essentially horizontally; and comprising a number of detent bolts (10,11);
(b) replaceable tabletop elements (3) positionable on said front and rear frame parts (4,5), each replaceable tabletop element (3) of the laboratory table (1) comprising detent openings (8,8',9,9') on a front side (66) and on a rear side (67) of the tabletop element (3), each of these detent openings (8,8',9,9') being implemented and arranged for insertion of a detent bolt (10,11); and
(c) fixing mechanisms (20) that are configured for fixing said replaceable tabletop elements (3) positioned on said front and rear frame parts (4,5) in a locking position,
wherein each replaceable tabletop element (3) is smaller in at least one horizontal dimension than said front and rear frame parts (4,5);
wherein each replaceable tabletop element (3) has a width (43) that at least approximately corresponds to a multiple of said regular distance (12) and that is configured as a modular tabletop element (3), which comprises at least four detent openings (8,8',9,9');
wherein the front frame part (4) and/or the rear frame part (5) of the laboratory table (1) comprise a number of detent bolts (10,11) that are arranged at a regular distance (12) defining a modular grid, each one of the detent bolts (10,11) being implemented and arranged for insertion into one of the detent openings (8,8',9,9') of the tabletop elements (3) positioned on these front and rear frame parts (4,5);
wherein said at least four detent openings (8,8',9,9') are arranged in groups, each group of detent openings (8,8',9,9') being linearly arranged and implemented for insertion of respective detent bolts (10,11) that are linearly arranged on said front and/or rear frame parts (4,5) of the laboratory table (1); and
wherein said at least four detent openings (8,8',9,9') are arranged at the same regular distance (12) or in a multiple of this regular distance (12).

30. The laboratory table (1) according to claim 29, wherein at least one detent opening (8,8',9,9') of the tabletop element (3) is configured as a slit (55) that extends from a front side (66) or from a rear side (67) of the tabletop element (3) and parallel to a tabletop axis (27) of the tabletop element (3).

31. The laboratory table (1) according to claim 29, wherein at least one detent opening (8,8',9,9') of the tabletop element (3) is configured as an oblong hole (15') that extends at a front side (66) or at rear side (67) of the tabletop element (3) and parallel to a tabletop axis (27) of the tabletop element (3).

32. The laboratory table (1) according to claim 29, wherein the front or rear frame part (4,5) of the laboratory table (1) comprises a fixing mechanism (20) configured as a lock profile (57) that is tiltable against a force of a spring (59) and about an axis (63), which spring (59) and axis (63) are fixed to the front or rear frame part (4,5) of the laboratory table (1).

33. The laboratory table (1) according to claim 32, wherein the lock profile (57) is configured and arranged to cover the detent openings (8,8',9,9') of the replaceable tabletop element (3) positioned on these front and rear frame parts (4,5) and to prevent the tabletop element (3) from vertical movements when the lock profile (57) is in a locking position.

34. The laboratory table (1) according to claim 29, wherein the detent bolts (10,11) of the laboratory table (1) are arranged at a regular distance (12) on a fixing mechanism (20) configured as a lock profile (57) that is tiltable against a force of a spring (59) and about an axis (63), which spring (59) and axis (63) are fixed to the front or rear frame part (4,5) of the laboratory table (1).

35. The laboratory table (1) according to claim 34, wherein the detent bolts (10,11) are configured and arranged to extend within the detent openings (8,8',9,9') of a replaceable tabletop element (3) positioned on these front and rear frame parts (4,5) and perpendicular to the tabletop element (3), thus preventing the tabletop element (3) from horizontal and vertical movements when the lock profile (57) is in a locking position.

36. The laboratory table (1) according to claim 29, wherein the fixing mechanism (20) is configured as a lock profile (57) that is attached to a front frame part (4) and/or to a rear frame part (5) of the laboratory table (1) in a way that the lock profile (57) in a lock position fixes all present replaceable tabletop elements (3) and prevents these tabletop elements (3) from horizontal and/or vertical movements.

* * * * *